US005580773A

United States Patent [19]

Kang et al.

[11] Patent Number: 5,580,773

[45] **Date of Patent: *Dec. 3, 1996**

[54] CHIMERIC IMMUNOGENIC GAG-V3 VIRUS-LIKE PARTICLES OF THE HUMAN IMMUNODEFICIENCY VIRUS (HIV)

[75] Inventors: Chil-Yong Kang; Lizhong Luo, both of London, Canada

[73] Assignee: Korea Green Cross Corporation, Kyongki-Do, Rep. of Korea

[ * ] Notice: The term of this patent shall not extend beyond the expiration date of Pat. No. 5,443,828.

[21] Appl. No.: 100,118

[22] Filed: Jul. 30, 1993

Related U.S. Application Data

[63] Continuation-in-part of Ser. No. 992,618, Dec. 18, 1992.

[30] Foreign Application Priority Data

Jun. 17, 1992 [KR] Rep. of Korea .................... 10493/92

[51] Int. Cl.$^6$ .................... C12N 7/04; A61K 39/21; G01N 33/53; C12P 21/06

[52] U.S. Cl. .................... 435/236; 424/188.1; 424/208.1; 435/5; 435/7.1; 435/974

[58] Field of Search .................... 424/184.1, 188.1, 424/192.1, 204.1, 207.1, 208.1; 435/69.3, 7.1, 235.1, 236; 530/350, 826; 536/23.72, 23.4

[56] References Cited

U.S. PATENT DOCUMENTS 4,925,784 6/1990 Crowl et al. .................... 435/5

OTHER PUBLICATIONS

Neurath, A. R. et al. Molecular Immunology 27(6): 529–49, 1990.

Luo, L et al. Proc. Natl. Acad. Sci USA 89: 10527–10531, 1992.

Gheyson et al., *Cell*, 59, 103–112 (1989).

Smith et al., *Virology*, 89, 517–527 (1978).

Carrow et al., *AIDS Res. and Hum. Retroviruses*, 7, 831–838 (1991).

Katzenstein et al., *J. AIDS*, 3, 810–816 (1990).

*Primary Examiner*—Robert D. Budens
*Assistant Examiner*—Jeffrey S. Parkin
*Attorney, Agent, or Firm*—Merchant, Gould, Smith, Edell, Welter, & Schmidt

[57] ABSTRACT

An unprocessed human immunodeficiency virus 2 (HIV-2) gag precursor protein, containing a deficient protease, assembles into virus-like particles by budding through the cytoplasmic domain of baculovirus-infected cells. Chimeric constructs were generated by coupling the truncated HIV-2 gag gene to the neutralizing domain (V3) or the neutralizing and CD4 binding domains (V3+CD4B) of gp120 env gene sequences obtained from HIV-1 or HIV-2. Virus-like particles were formed by chimeric gene products when the env gene sequences were linked to the 3' terminus of the gag gene. The gag-env chimeric proteins displayed immunoreactivity towards anti-gp120 rabbit antisera.

8 Claims, 18 Drawing Sheets

| MA p16 | CA p26 | NC p12 | HIV-2 GAG (519aa) |

MUTANTS | PARTICAL FORMATION

HIV2-gag 366  3'—AATATCCGTCTTCGGATCCCTAGGCGCG—5'
                              ↑1970  TT BamHI
              ↑1956

HIV2-gag 344  —

HIV2-gag 322  3'—TGGGTTTGTGACGATATCCCTAGGCGCG—5'
                              ↑1839  TT BamHI
              ↑1825

HIV2-gag 304  3'—AAGATGTTTCGAACATCCCTAGGCGCG—5'
                              ↑1785  TT BamHI
              ↑1771

SITE-SPECIFIC MUTAGENESIS

| MUTANT | | 373 375 377 | PARTICLE FORMATION |
|---|---|---|---|
| HIV2-gag380-W | N———————————— | CCA CCC CCA C / Pro Pro Pro | + |
| HIV2-gag380-1 | N———————————— | CCA CCC CTA C / Pro Pro Le

HIV-1 gp120 GENE IN pUC19

HIV-2 gp120 GENE IN pUC18

Creation of BglII site by crossover linker mutagenesis

HIV-2 GAG

Insertion of gp120 BglII fragment into BglII site of gag gene

A. Antiserum against HIV-1 gp120

B. Antiserum against HIV-2 gp120

A. HIV-1 four neutralizing epitopes:
1: 304-318 (V3) 15 aa
2: 489-503 (C-terminus of gp120) 15 aa
3: 652-666 (gp41) 15 aa
4: 732-746 (gp41) 15 aa

B. Consensus Sequence (CS) of HIV-1 V3 loop:
TRKSIHIGPGRAFYTTGE 18 aa (18 x 3 = 54 aa)

C. Different HIV-1 Isolates (V3):

IIIB: 15 aa
MN: 15 aa
SF2: 15 aa
RF: 15 aa

FIG. 10A

<u>Bgl</u>II | 304-318 (V3 loop)
GATCT | AGA AAA AGC ATC CGT ATC CAG AGA GGA CCA GGG AGA GCA

| 489-503 (C-terminus of gp120)
TTT GTT | GTA AAA ATT GAA CCA TTA GGA GTA GCA CCC ACC

| 652-666 (gp41)
AAG GCA AAG AGA | CAG CAA GAA AAG AAT GAA CAA GAA TTA

| 732-746 (gp41)
TTG GAA TTA GAT AAA TGG | GGA ATA GAA GAA GAA GGT GGA

| <u>S</u> <u>Bam</u>HI <u>Sph</u>I
GAG AGA GAC AGA GAC AGA TCC ATT | TAG GGATCC GCATG

FIG. 10B

<u>Bgl</u>II | (V3 loop)
GATCT | ACC AGA AAA AGC ATC CAT ATC GGA CCA GGG AGA GCA TTT

| (V3 loop)
TAT ACA ACA GGA GAA | ACC AGA AAA AGC ATC CAT ATC GGA

| (V3 loop)
CCA GGG AGA GCA TTT TAT ACA ACA GGA GAA | ACC AGA AAA

AGC ATC CAT ATC GGA CCA GGG AGA GCA TTT TAT ACA ACA

| <u>S</u> <u>Bam</u>HI <u>Sph</u>I
GGA GAA | TAG GGATCC GCATG

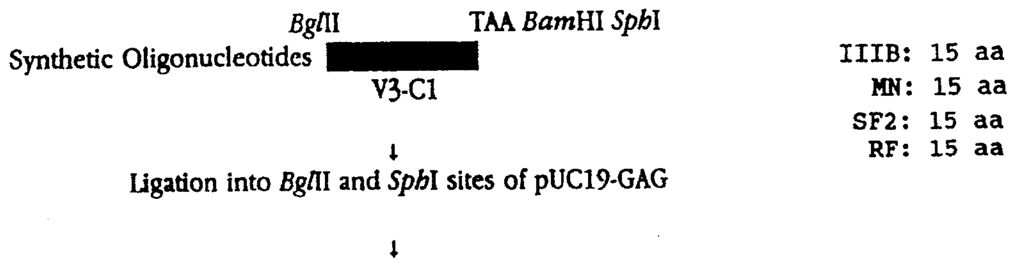
FIG. 11A
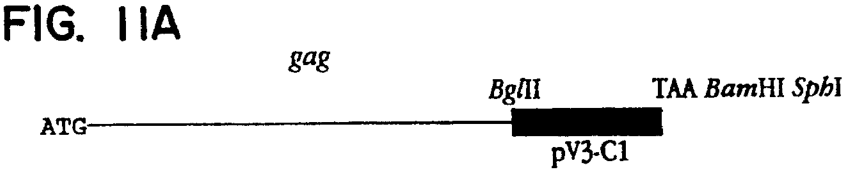
FIG. 11B
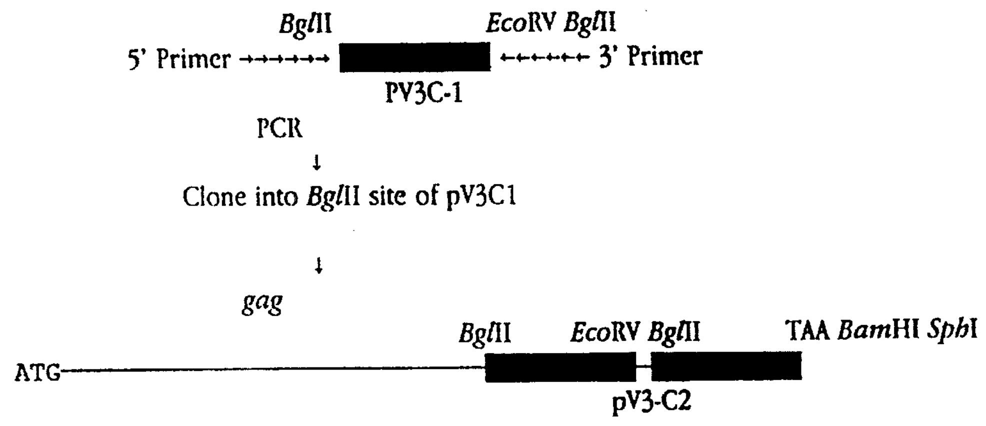
FIG. 11C
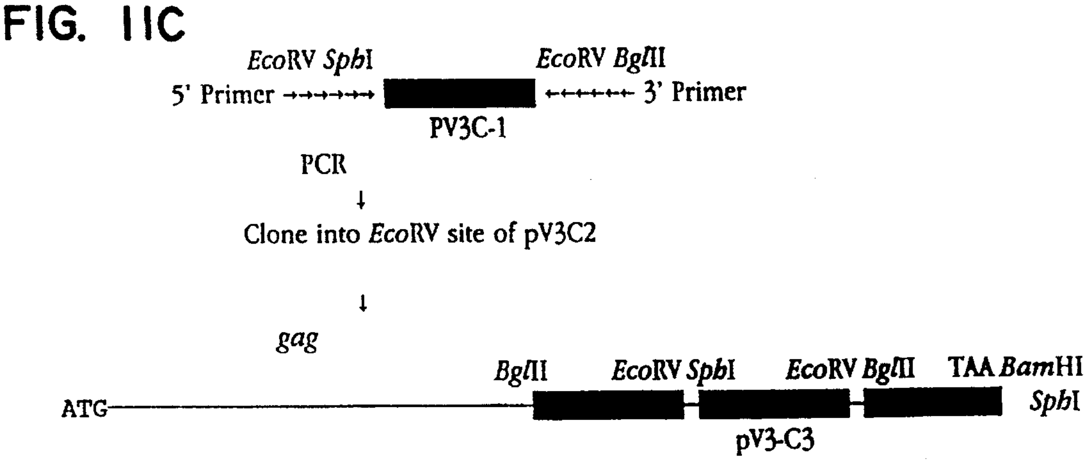

FIG. 12A

*Bgl*II | (IIIB V3 loop)
GATCT | AGC ATC CGT ATC CAG AGA GGA CCA GGG AGA GCA TTT GTT ACA ATC | (MN V3 loop) AAA AGA ATC CAT ATC GGA CCA GGG AGA GCA TTT TAT ACA ACA AAG | (SF2 V3 loop) AGC ATC ACA AAG GGA CCA GGG AGA GTA ATC TAT GCC ACA GGA CAG | (RF V3 loop) AGC ATC TAT ATC GGA CCA GGG AGA GCA TTT CAT ACA ACA GGG AGA | S *Bam*HI *Sph*I
TAG GGATCC GCATG

FIG. 12B

*Bgl*II | (IIIB V3 loop)
GATCT | AGC ATC CGT ATC CAG AGA GGA CCA GGG AGA GCA TTT GTT ACA ATC | (MN V3 loop) AAA AGA ATC CAT ATC GGA CCA GGG AGA GCA TTT TAT ACA ACA AAG | (SF2 V3 loop) AGC ATC ACA AAG GGA CCA GGG AGA GTA ATC TAT GCC ACA GGA CAG | (RF V3 loop) AGC ATC TAT ATC GGA CCA GGG AGA GCA TTT CAT ACA ACA GGG AGA | *Eco*RV *Bgl*II
GATATC AGATCT |

(IIIB V3 loop)
AGC ATC CGT ATC CAG AGA GGA CCA GGG AGA GCA TTT GTT

ACA ATC | (MN V3 loop) AAA AGA ATC CAT ATC GGA CCA GGG AGA GCA TTT

TAT ACA ACA AAG | (SF2 V3 loop) AGC ATC ACA AAG GGA CCA GGG AGA GTA

ATC TAT GCC ACA GGA CAG | (RF V3 loop) AGC ATC TAT ATC GGA CCA GGG

AGA GCA TTT CAT ACA ACA GGG AGA | S *Bam*HI *Sph*I
TAG GGATCC GCATG

FIG. 13

```
BglII        (IIIB V3 loop)
GATCT  | AGC ATC CGT ATC CAG AGA GGA CCA GGG AGA GCA TTT GTT

                     (MN V3 loop)
       ACA ATC | AAA AGA ATC CAT ATC GGA CCA GGG AGA GCA TTT

                        (SF2 V3 loop)
       TAT ACA ACA AAG | AGC ATC ACA AAG GGA CCA GGG AGA GTA

                             (RF V3 loop)
       ATC TAT GCC ACA GGA CAG | AGC ATC TAT ATC GGA CCA GGG

                                       EcoRV    SphI
       AGA GCA TTT CAT ACA ACA GGG AGA | GATATC GCATGC |

            (IIIB V3 loop)
       AGC ATC CGT  ATC CAG AGA GGA CCA GGG AGA  GCA TTT GTT

                     (MN V3 loop)
       ACA ATC | AAA AGA ATC CAT ATC GGA CCA GGG AGA GCA TTT

                        (SF2 V3 loop)
       TAT ACA ACA AAG | AGC ATC ACA AAG GGA CCA GGG AGA GTA

                             (RF V3 loop)
       ATC TAT GCC ACA GGA CAG | AGC ATC TAT ATC GGA CCA GGG

                                       EcoRV    BglII
       AGA GCA TTT CAT ACA ACA GGG AGA | GATATC AGATCT |

            (IIIB V3 loop)
       AGC ATC CGT  ATC CAG AGA GGA CCA GGG AGA  GCA TTT GTT

                     (MN V3 loop)
       ACA ATC | AAA AGA ATC CAT ATC GGA CCA GGG AGA GCA TTT

                        (SF2 V3 loop)
       TAT ACA ACA AAG | AGC ATC ACA AAG GGA CCA GGG AGA GTA

                             (RF V3 loop)
       ATC TAT GCC ACA GGA CAG | AGC ATC TAT ATC GGA CCA GGG

                                       S  BamHI   SphI
       AGA GCA TTT CAT ACA ACA GGG AGA | TAG GGATCC GCATG
```

CHIMERIC IMMUNOGENIC GAG-V3 VIRUS-LIKE PARTICLES OF THE HUMAN IMMUNODEFICIENCY VIRUS (HIV)

CROSS-REFERENCE TO RELATED APPLICATIONS

This patent application is a continuation-in-part of U.S. patent application Ser. No. 07/992,618, filed Dec. 18, 1992.

FIELD OF THE INVENTION

The present invention relates to construction of chimeric proteins useful for an AIDS vaccine and the development of diagnostic reagents, and a process for production thereof. More particularly, the present invention relates to gag chimeric proteins of HIV expressed in a recombinant baculovirus-infected insect cell, and a process for production thereof.

BACKGROUND OF THE INVENTION

Type 1 and 2 of the human immunodeficiency viruses (HIV) are recognized as the etiologic agents for acquired immunodeficiency syndrome (AIDS). A vaccine against these viruses would be an ideal way of preventing infection with HIV and AIDS. Accordingly, much research has been focused on molecular biological analyses of structures and functions of HIV. The main virion structural proteins of HIV are derived from three structural genes known as gag, pol, and env. The genome of many different isolates of HIV have been completely sequenced, and amino acid sequences have been deduced from the cloned proviral DNA sequences. The envelope gene of HIV codes for a glycoprotein precursor with a molecular weight of 160,000 (gp160). The precursor gp160 in virus-infected cells is processed (or cleaved) to produce envelope glycoprotein gp120 and gp41. The envelope glycoproteins gp120 of HIV has been the major target for developing a candidate vaccine against AIDS. gp120 recognizes the cellular receptor (CD4) on helper T lymphocytes, and carries the V3 loop domain that induces neutralizing antibodies (Putney et al., *Science* 234, 1392–1395 (1986); Robey et al., *Proc. Natl. Acad. Science, USA* 83, 7023–7027 (1986)).

The V3 loop represents the third hypervariable region of HIV-1 gp120 (amino acid residues 308–331) which contains not only a major immunodominant neutralizing epitope but also the epitopes for antigen-dependent cellular cytotoxicity (ADCC) and cytotoxic T-lymphocyte (CTL) recognition. Although the majority of the amino acids in the V3 loop are variable among different strains of HIV, a G-P-G-R motif at the tip of the loop is conserved (LaRosa et al., *Science* 249, 932–935 (1990)).

Recently, Huang et al. and Björling et al. demonstrated that the principal neutralization domain of the envelope glycoprotein of HIV-2 is also located in the region corresponding to the hypervariable motif in the V3 loop of HIV-1 gp120 (Huang et al., *J. Virol.* 65,5073–5079 (1991); Bj örling et al., *Proc. Natl. Acad. Sci. USA* 88, 6082–6086 (1991). The CD4-binding region, located within C-terminal third of HIV-1 gp120 (amino acid residues 397–439), plays an essential role in the infectivity of HIV. This region also seems to be weakly immunogenic because it forms a pocket which is not accessible to the immune system, and, therefore, high-titre neutralizing antibody against this region is not presently available.

SUMMARY OF THE INVENTION

The present invention is directed to gag-env chimeric proteins, an anti-HIV vaccine containing the chimeric proteins, gag-env chimeric genes, recombinant baculoviruses carrying the HIV gag-env chimeric gene, and methods of making and using the genes and proteins. The gag-env chimeric proteins may be obtained by linking gag of HIV-2 to env of HIV-1 and HIV-2 to form a gag-env chimeric gene, inserting the chimeric gene into the DNA genome of a baculovirus, expressing the recombinant chimeric proteins in a host cell such as an insect cell, and culturing and purifying the resulting chimeric protein. The chimeric proteins provided according to the invention are useful in an anti-AIDS vaccine.

Other objects, features and advantages of the invention will hereinafter become more readily apparent from the following description.

BRIEF DESCRIPTION OF THE DRAWINGS

FIG. 9 shows the design of chimeric gag containing multiple neutralizing epitopes.

FIG. 10 show two chimeric gag-env gene constructs. FIG. 10A shows Construct A [SEQ ID NO:7], a chimeric gag-env gene containing four neutralizing epitopes at the 3' terminus of HIV-2 gag gene, which produced virus-like particles and induced neutralizing antibodies. FIG. 10B shows Construct B [SEQ ID NO:8], a chimeric gag-env gene containing the consensus sequences (CS) of HIV-1 V3 loop region (54 amino acids) in tandem, which produced virus-like particles and provided a stronger immune response.

FIG. 11 shows different HIV-1 isolates with V3 epitopes, and a scheme of linking multiple V3 epitopes. FIG. 11A, Construct V3C1; FIG. 11B, Construct V3C2; and FIG. 11C, Construct V3C3.

FIG. 12 shows the sequences of Constructs C1 and C2. FIG. 12A, single construct C1 containing the V3 loop of four different HIV-1 isolates (60 amino acids) [SEQ ID NO:9]; FIG. 12B, Construct C2 containing double construct C1 [SEQ ID NO:10]. Constructs C1 and C2 formed virus-like particles.

FIG. 13 shows the sequence of Construct C3 [SEQ ID NO:11] containing triple construct C1. This construct formed virus-like particles.

DETAILED DESCRIPTION OF THE INVENTION

The present invention provides gag chimeric proteins of HIV which retain both antigenic and immunogenic properties of gag, in combination with a portion of one or more env proteins. It has been reported previously that expression of the gag coding sequences of HIV-2 lacking the protease gene in insect cells produced virus-like particles (Luo, L.T. and C.Y. Kang, *Virology* 179, 874–880 (1990)). It has now been found that the C-terminus of the gag protein, including the zinc finger domain, is not necessary for particle formation (see FIG. 1). Therefore, according to the invention, the C-terminus of the gag precursor protein may be replaced with other sequences without losing the ability of the gag protein to form virus-like particles. The gag protein has the unique ability to form particles in the absence of all other components of the virus, and the chimeric gag particles are devoid of genomic RNA.

Formation of chimeric gag particles, according to the invention, which contain the major neutralizing epitope (V3) and/or the CD4-binding domain (CD4BD) of gp120, provides for the generation of HIV-neutralizing antibodies. Antigens presented in a particulate form may enhance immunogenicity of the epitopes, and multiple copies of specific epitopes can be presented. Furthermore, secreted chimeric particles can be safely and easily collected and purified from a cell culture media by centrifugation, or other like means known and used in the art.

The present invention provides mapping of essential domains of gag protein for particle formation, and the construction of chimeric gag genes containing either the V3 loop (V3) or the V3 loop plus the CD4 binding domain (V3+CD4BD) of gp120 from HIV-1 or HIV-2. These constructs were expressed in insect cells using a baculovirus expression vector. The chimeric gene construction indicates that only certain combinations of fusion proteins are expressed, assembled as virus-like particles, and retain antigenicity and immunogenicity of both gag and env epitopes.

Figure 1:
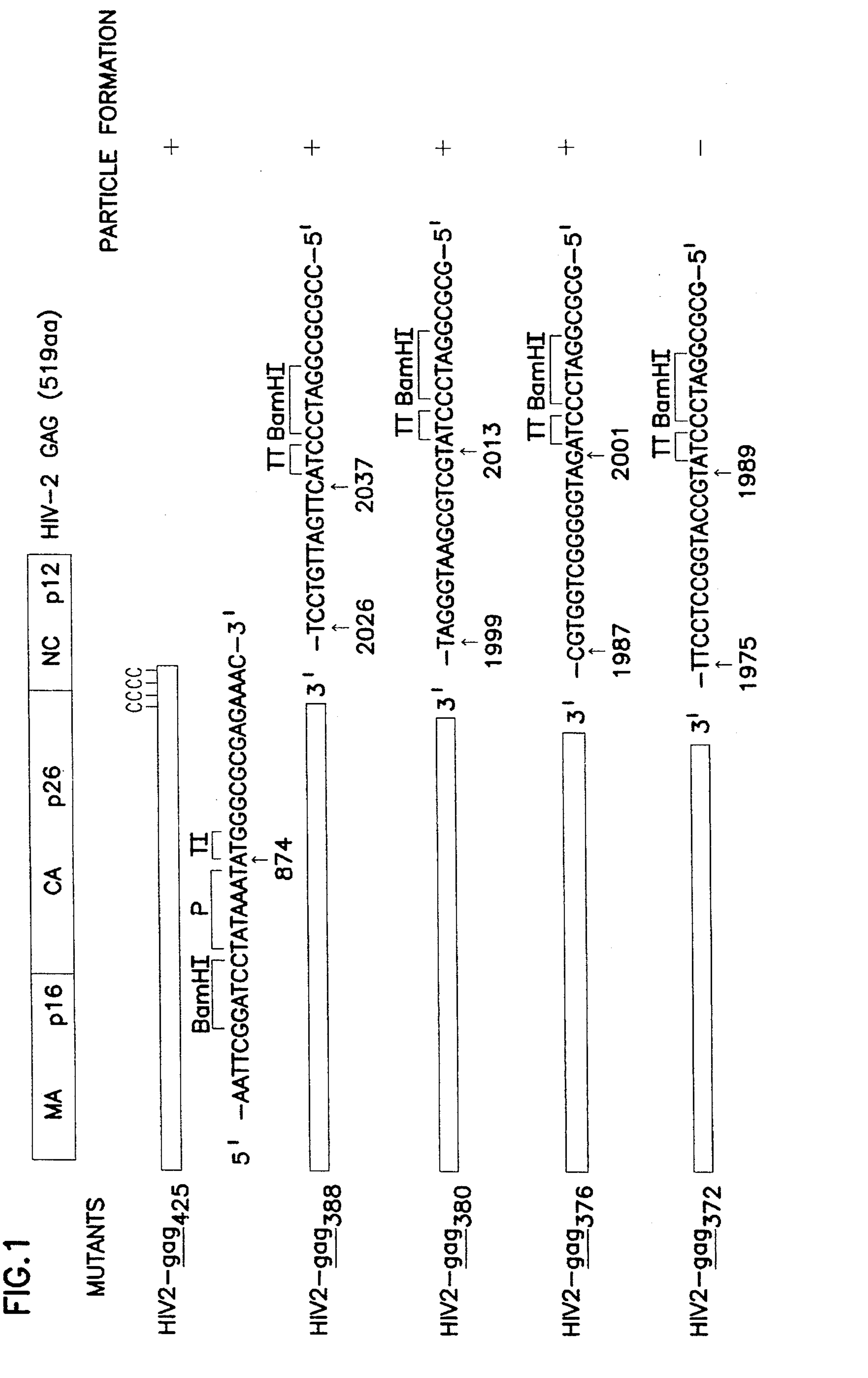
FIGS. 1 and 1A show deletion mutants of HIV-2 gag gene and particle formation. A series of deletion mutants of HIV-2 gag gene were constructed by polymerase chain reaction (PCR) with specific primers and the size of the deletion mutant are indicated by the amino acid numbers which are retained. Deletion mutants of HIV-2-$gag_{425}$ [SEQ ID NO:12], -$gag_{388}$ [SEQ ID NO:13], -$gag_{380}$ [SEQ ID NO:14], and -$gag_{376}$ [SEQ ID NO:15]formed virus-like particles released into culture medium, whereas deletion mutants HIV-2-$gag_{372}$ [SEQ ID NO:16], -$gag_{366}$ [SEQ ID NO: 17], -$gag_{344}$, -$gag_{322}$ [SEQ ID NO:18], and -$gag_{304}$ [SEQ ID NO:19], did not. Polypeptide domains of HIV-2 gag protein, p16 MA (matrix protein), p26 CA (capsid protein) and p12 NC (nucleic acid binding protein) are shown on the top of diagram. The "C's" on HIV-$gag_{425}$ denote cysteine which represent the zinc finger domain.
Figure 1A:
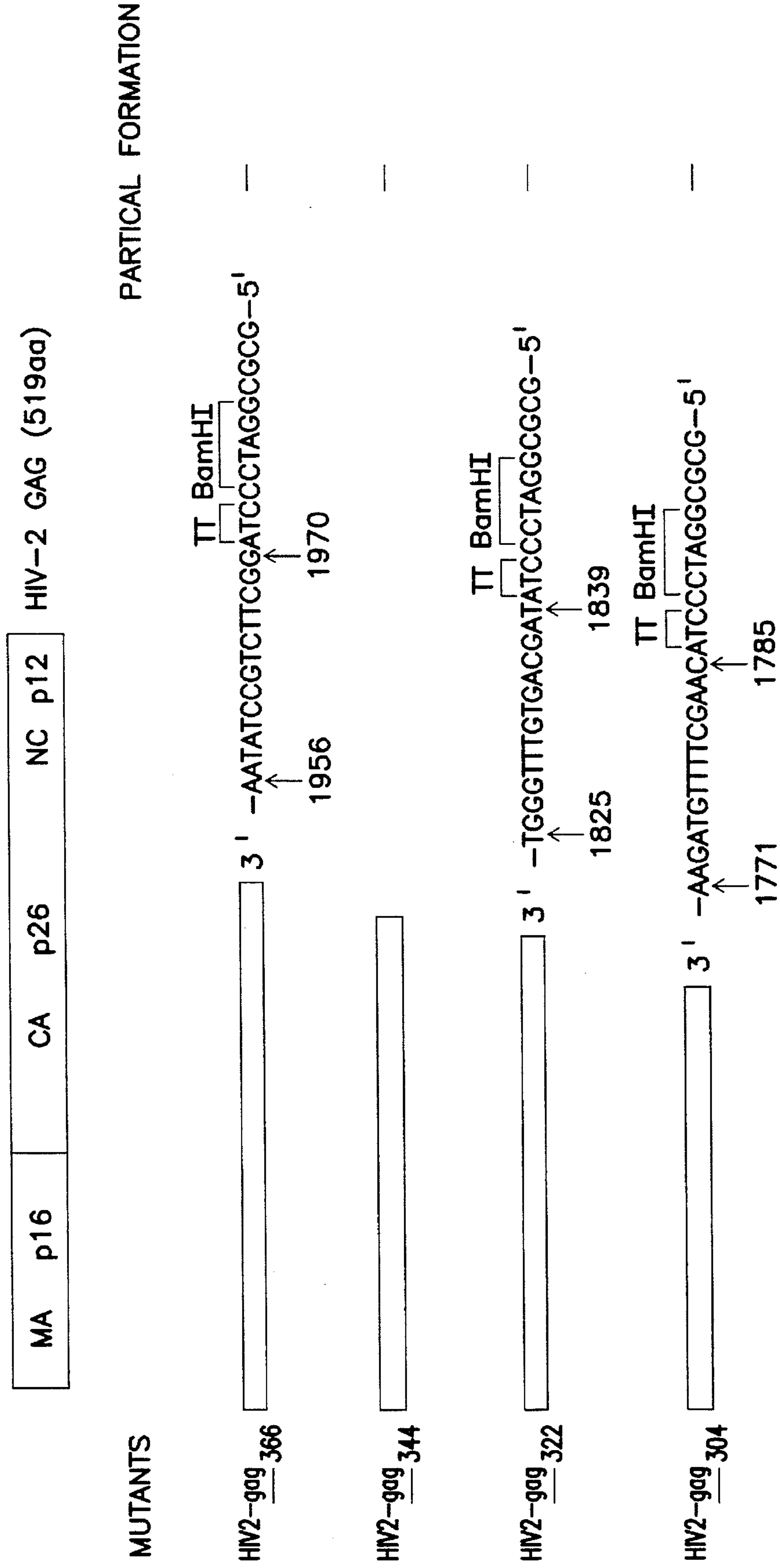
Figure 2:
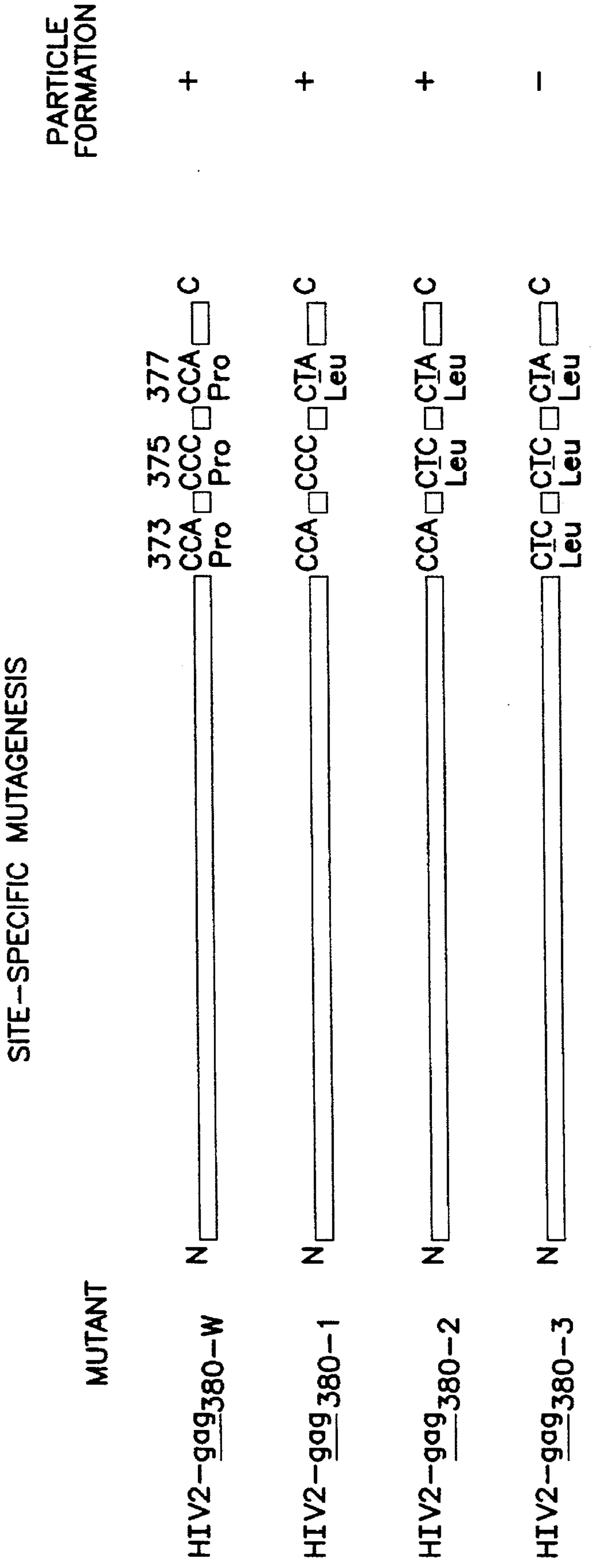
FIG. 2 shows site-specific mutants of HIV-2-$gag_{380\text{-}W}$ gene with particle formation. Three prolines located at amino acid position 373, 375 and 377 at the C-terminus of gag mutant, HIV-2-$gag_{380\text{-}W}$, were substituted with 1, 2 or 3 leucine residues by site-directed mutagenesis using PCR, and expressed in SF9 cells. The substitution of up to two prolines did not affect the gag particle formation, whereas changing of all three prolines resulted in the failing of particle formation, as examined by electron microscopy.

Up to about 198 amino acids have been added at the carboxyl-terminus of HIV-2-$gag_{425}$ which represents 425 amino acids of gag including the zinc finger structure. One author reported that truncation of HIV-1 gag precursor protein by deletion of p15 fails to assemble virus-like particles after expression by baculovirus vector, suggesting that some amino acids at the C-terminus p15 polypeptide of HIV-1 gag are critical for particle formation (Gheyson et al., *Cell* 59:112, 1989). It has now been found, however, that HIV-2 $gag_{388}$ formed gag particles with only 388 amino acids and without the zinc finger domain (see FIG. 1). To map the minimum length of HIV-2 gag gene sequence and functional domain of HIV-2 gag precursor protein required for gag particle formation, a series of truncated, or deletion mutants of HIV-2 gag genes were constructed, as shown in FIG. 1, and site-directed mutagenesis was carried out. It was found that the minimum sequence length of HIV-2 gag for forming an HIV-2 gag particle is 376 amino acids at the N-terminus (see FIG. 1). Particle formation was eliminated by the deletion of an additional four amino acids at the C-terminus which represents the 372 amino acids at the N-terminus. Up to 143 amino acids may be deleted at the C-terminus from the 519 amino acid sequence. It was further found that, in contrast to previous reports, the zinc-finger domain at the C-terminus is not required for gag particle formation. Site-directed mutagenesis also revealed that at least one proline at amino acid positions 373rd, 375th or 377th is essential for particle formation, as shown in FIG. 2. As further illustrated in FIGS. 1 and 2, retention of an uninterrupted 1,128 base pairs of HIV-2 gag reading frame is essential to express foreign epitopes into gag particles.

The chimeric HIV gag-env genes of the invention may be constructed by coupling the truncated HIV-2 gag gene which will code for at least about 376 amino acids to the neutralizing domain (V3), or neutralizing domain (V3) and the CD4-binding domain (V3+CD4BD) of gp120 env gene sequence from HIV-1 or HIV-2. To construct such a chimeric gene, the env gene sequences may be either inserted into the middle of the gag gene or at the 3' terminus of the gag gene. Virus-like particles were formed by chimeric gene products only when the env gene sequences were linked to the 3' terminus of the gag gene. Insertion of the env gene sequence in the middle of the gag gene resulted in high level chimeric gene expression but without the formation of virus-like particles.

It was found that interruptions of the gag open reading frame in the middle of the gene by insertion of foreign epitopes destroys the ability to form particles, and that the N-terminal sequences of gag precursor are necessary for membrane association and virus assembly. It was further found that mutations of the glycine codon abolished myristylation, and eliminated membrane association, capsid formation and budding. Therefore, it is preferred that foreign epitopes are provided at the carboxyl-terminus of the gag protein.

Three chimeric proteins, (1) gag (425 amino acids) combined with HIV-1 V3 (91 amino acids), (2) gag with HIV-2 V3 (90 amino acids), and (3) gag with HIV-2 V3+CD4BD (198 amino acids), formed virus-like particles that were secreted into the cell culture medium, as shown in Table 1 below.

TABLE 1

| | Comparison of particle formation and yield of chimeric fusion proteins | | |
|---|---|---|---|
| Recombinant Viruses | Particle formation* | Sucrose concentration** | Yield/5 × $10^8$ cell/liter |
| AcNPV-HIV-2gag | + | 40% | 30 mg |
| Ac-gagM-1V3 | – | — | — |
| Ac-gagC-1V3 | + | 50% | 6 mg |
| Ac-gagM-2V3 | – | — | — |
| Ac-gagC-2V3 | + | 50% | 25 mg |
| Ac-gagC-2V3 + 2CD4BD | + | 60% | 2 mg |

*Plus sign denotes virus-like particles were recovered from the cell culture media.
**Virus-like particles were banded on top of the sucrose solution after ultracentrifugation.

The invention is further directed to a chimeric gag-env gene containing multiple neutralizing epitopes of HIV envelope glycoproteins attached at the 3' terminus of the gag gene, and peptides produced by the chimeric gene. Preferably, the chimeric gene is constructed with two, preferably three, more preferably four env genes encoding for virus-neutralizing domains of gp120 and/or gp41 of HIV. For example, the chimeric gene may include the gene sequence encoding for the third-variable (V3) region of gp120 of HIV-1 (amino acids 304–318), the C-terminal end of gp120 of HIV-1 (amino acids 489–508), the conserved region of gp41 of HIV-1 (amino acids 652–666), and/or the conserved region in the intracellular part of gp41 of HIV-1 (amino acids 732–746). The resulting constructs produce virus-like particles which are capable of inducing neutralizing antibodies against HIV.

Another gag-env chimeric gene according to the invention contains an HIV gag sequence linked to multiple V3 coding sequences from the consensus sequence of HIV V3 loop of gp120, and proteins produced by the gene. Yet another gag-env chimeric gene contains multiple V3 domains derived from multiple HIV variants, as for example, isolates HIV-$1_{IIIB}$, HIV-$1_{mn}$, $HIV_{SF2}$, HIV-$1_{RF}$ and HIV-$2_{NIH-Z}$. Such a gene is useful for generating neutralizing antibodies for multiple variants of HIV in the population.

The chimeric genes may be expressed in insect cells using recombinant baculoviruses. The resulting chimeric gag peptides may then be purified by a discontinuous sucrose gradient centrifugation method, or by other like methods known and used in the art. The purified peptide may then be used, for example, in a vaccine to immunize a mammal for producing anti-HIV antibodies.

Also provided are recombinant baculoviruses transformed with a chimeric gag-env gene of the invention. A recombinant baculovirus may be prepared, for example, from Autographa Californica nuclear polyhedrosis virus (AcNPV), Bombyx iridexcent virus, or other like baculovirus. To provide a recombinant virus according to the invention, a chimeric gag-env gene is inserted into the baculovirus genome by homologous recombination, and purified, for example, by a consecutive plaque assay or other suitable method known and used in the art to select a polyhedrin negative recombinant virus. Examples of recombinant viruses suitable for use according to the invention have been placed on deposit with American Type Culture Collection (ATCC) (Feb. 26, 1991). These include AcNPV containing gag of HIV-2 (ATCC deposit no. VR2314); AcNPV containing gag of HIV-2 and V3 of HIV-1 (ATCC deposit no. VR2316); AcNPV containing gag of HIV-2 and V3 of HIV-2 (ATCC deposit no. VR2317); AcNPV containing gag of HIV-2 and four neutralizing epitopes (construct A; ATCC deposit no. VR2423); AcNPV containing gag of HIV-2 and consensus sequences of HIV-1 V3 loop in tandem (construct B; ATCC deposit no. VR2425); and AcNPV containing gag of HIV-2 and V3 loops of four different HIV-1 isolates (construct C; ATCC Deposit No. VR2424). The deposits are guaranteed to be furnished on request for the purpose of research.

To express the gag chimeric protein, a host cell, preferably an insect cell, is infected with the recombinant baculovirus. For example, the recombinant baculovirus may be infected into *Spodoptera frugiperda* cells, *Mamestra brassica* cells, *Trichoplusia ni* cells, *Bombyx mori* cells, or other AcNPV-susceptible insect cells.

The expressed chimeric gag particles have been shown to elicit neutralizing antibodies in rabbits which completely block HIV infection. The chimeric gag particles produced according to the invention, are useful as antigens in an anti-AIDS vaccine, in a diagnostic reagent formulation, and the like. An anti-AIDS vaccine prepared with the chimeric gag particles of the present invention, is useful for providing a specific immune reaction against an immunogen. The vaccine may be used at pre- or post- exposure to prevent infection of HIV, or may be used in an immunotherapeutic treatment. A vaccine preparation may include a conventional absorbent, stabilizer, adjuvant, carrier, and the like, as known and used in the art, and may be administered to a patient, including a human or other mammal, through a conventional route.

The invention will be further described by reference to various specific and preferred embodiments and techniques. These examples are not meant to limit the scope of the invention that has been set forth in the foregoing description. It should be understood that many variations and modifications may be made while remaining within the spirit and scope of the invention, as would be apparent to those skilled in the art. The disclosures of the cited references throughout the application are incorporated by reference herein.

EXAMPLE 1

Preparation of Plasmids

Autographa californica nuclear polyhedrosis virus (AcNPV) and recombinant AcNPV were grown and assayed in *Spodoptera frugiperda* (SF9) cell monolayers using complete TNM-FH medium containing 10% fetal bovine serum at 27° C. as described by C.Y. Kang, *Adv. Virus Res.* 35, 177–192 (1988). Wild type AcNPV DNA was purified by the method of G.E. Smith and M.D. Summers, *Virology* 89,517–527 (1978).

Plasmids pHXB-2D and plBM containing the entire HIV-$1_{HXB2D}$ and HIV-$2_{NIHZ}$ genomes, respectively, were obtained from Dr. R. Gallo (National Institutes of Health, Bethesda, Md.). The recombinant plasmids pUC19-gp120-NSS, pUC18-gp120 and pUC19-GAG containing full-length cDNA copies of the HIV-1 env, HIV-2 env and a truncated gag gene of HIV-2 (which codes 425 amino acids), respectively, were subcloned from pHXB-2D and p1BM as described by the inventors in *Virology* 179, 874–880 (1990).

EXAMPLE 2

Preparation of Chimeric Gene

To subclone the V3 and V3+CD4B of the HIV-1 and HIV-2 env genes into a pUC19-GAG recombinant, plasmids pUC19-gp120-NSS and pUC19-gp120 were used as a template and the specific regions were amplified with appropriate oligonucleotide primers. That is, plasmids pUC19-gp120-NSS (HIV-1) and pUC18-gp120 (HIV-2) were used as templates for polymerase chain reaction (PCR) amplification of an HIV-1 DNA fragment corresponding to V3 domain (91 amino acids, position 273–363) and HIV-2 DNA fragments corresponding to V3 equivalent domain (90 amino acids, position 294–383) and V3+CD4BD (198 amino acids, position 294–491). All primers were designed to create a BglII restriction site such that gp120 DNA fragments could be inserted into the BglII site of pUC19-GAG.

The HIV-1 V3 DNA fragment was amplified using primer L-1: (5'-CGAAGATCTGTCAATTTCACGG-3') [SEQ ID NO:1] and primer L-2:(5'-GCAGATCTTTGCTTAAA-GATTA-3') [SEQ ID NO:2], which are complementary to nucleotides 816 through 836, and 1075 through 1089, respectively. The V3+CD4BD DNA fragment of HIV-1 was generated from pUC19-gp120-NSS BglII digestion at nucleotide positions 816 and 1398 of gp120. Primers L-3:(5'-CGAGATCTCATTGTAAGAGGCC-3') [SEQ ID NO:3], and L-4 (5'-GCAGATCTTCTGCAGTTAGTCC-3') [SEQ ID NO:4], complementary to nucleotides position 879 through 893, and 1135 through 1149 of HIV-2 gp 120, respectively, were used to synthesize the HIV-2 V3 DNA fragment. Primers L-3 and L-5 (5'-GCAGATCTCTTTACT-GATGTAG-3') [SEQ ID NO:5], which is complementary to nucleotides 1459 through 1473 of HIV-2 gp120, were used to synthesize the HIV-2 V3+CD4BD DNA fragment. PCR was performed according to the procedures provided with the Geneamp kit (Norwalk, Conn.). Briefly, 20 ng of linearized gp120 DNA was added to 100 μl PCR reaction mixture (10 mM Tris-HCl, 50 mM KCl, 1.5 mM $MgCl_2$, and 0.01% gelatin) containing 20 μM each dNTP, 2.5 Units of Taq polymerase, and 20 μM of each oligonucleotide primer.

Figure 3:
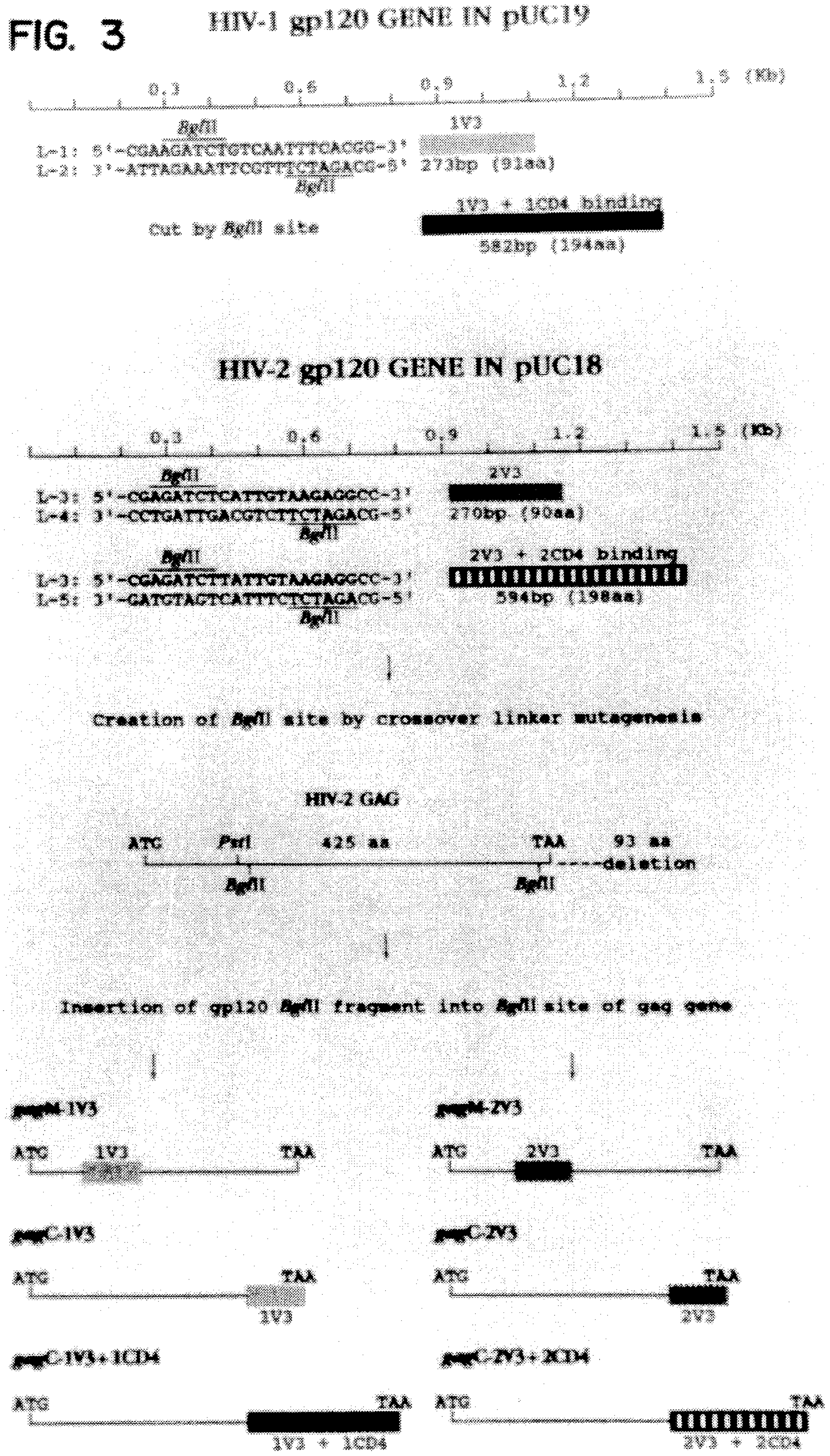
FIG. 3 shows construction of chimeric gag-env genes. BglII fragments containing the V3 (amino acid positions 273–363) or V3+CD4BD (amino acid position 294–491) from HIV-2 gp120 were amplified by PCR. The V3+CD4BD sequences of HIV-1 was directly isolated from pUC-gp120-NSS by BglII digestion. To insert these BglII fragments at the 3'-terminus of the HIV-2 gag gene without the protease sequences, two BglII sites were created by crossover linker mutagenesis, one downstream of the PstI site and another at the C-terminus just upstream of the stop codon. BglII fragments carrying either V3 or V3+CD4BD from HIV-1 or HIV-2 were inserted into either the middle of the 3' terminal BglII site. Six constructs were made. The dot-hatched box and solid black box represent the V3 and CD4BD of HIV-1 gp120, respectively. The checkered box and the box with vertical lines represent the V3 and V3+CD4BD of HIV-2 gp120, respectively. The number of amino acids presented in each fragment is indicated.

The V3 and V3+CD4BD genes were amplified for 30 PCR cycles (94° C. for 1 min., 45° C. for 3 min.). The chimeric gag gene constructs containing the V3 and V3+CD4BD fragments were confirmed by dideoxy DNA sequencing of double stranded DNA, using the Sequence Kit™ (U.S. Biochemical Corporation).

gagM-1V3, gagC-1V3, gagC-1V3+1CD4BD, gagM-2V3, gagC-2V3, gagC-2V3+2CD4BD chimeric genes were prepared by the above-described method. The numbers 1 and 2 in front of V3 and CD4BD denote genes from HIV-1 and HIV-2 respectively, gagM denotes the chimeric gene inserted into the middle of the gag gene, and gagC denotes the chimeric gene inserted into the terminus of the gag gene. The procedure for generation of the present chimeric gene is shown in brief in FIG. 3.

EXAMPLE 3

Production of Recombinant Baculovirus

The chimeric genes obtained in Example 2 were isolated after digestion with BamHI and inserted into the baculovirus transfer vector pAcYM1. SF9 cells were co-transfected with mixtures of infectious wild type AcNPV DNA (1 μg) and recombinant plasmid DNAs (4 μg) using standard procedures as described in C.Y. Kang, *Adv. Virus Res.*, 35, 177–192, (1988).

Among the recombinant baculoviruses obtained from the above-described procedure, the following were deposited with the American Type Culture Collection (ATCC) on Feb. 26, 1991, guaranteed for furnishing samples for the purpose of research: AcNPV carrying gag of HIV-2 (hereinafter called 'AcHIV2GAGYK') was deposited as deposit number VR2314, AcNPV carrying gag of HIV-2 and V3 of HIV-1 (hereinafter called 'AcHIV2GAG+1V3YK') as deposit number VR2316, and AcNPV carrying gag of HIV-2 and V3 of HIV-2 (hereinafter called 'AcHIV2GAG+2V3YK') as a deposit number VR2317.

After incubation of recombinant baculovirus at 27° C. for 4 days, culture supernatants were harvested and titrated on 80% confluent monolayers of SF9 cells. To obtain polyhedrin-negative recombinant AcNPV, the plaques lacking polyhedra were picked, purified by three consecutive plaque assays, and used to produce virus stock of $2\times10^8$ PFU/ml.

EXAMPLE 4

Expression of Chimeric Particles

SF9 cells were infected with either wild type AcNPV or recombinant AcNPV carrying chimeric genes at multiplicities of infection of 5 PFU/cell, and incubated at 27° C. After appropriate incubation times (3 to 4 days), cells were harvested and washed twice with phosphate buffered saline (PBS). Whole cell lysates were prepared by resuspending the cell pellet in water and adding an equal volume of 2× dissociation buffer (10% beta-mercaptoethanol, 10% SDS, 25% glycerol, 100 mM Tril-HCl, pH 7.0, 0.04% bromophenol blue). Cell lysates were analyzed by electrophoresis in 12% polyacrylamide gel containing SDS (SDS-PAGE) and the protein bands were visualized by staining with Coomassie blue according to the method described in *Nature* 227, 283–303 (1987). Western blot analyses were then performed using sera from AIDS patients and the Bio-Rad Immune Blot AK system. The results are shown in FIG. 4.

Figure 4B:
FIG. 4 shows expression of chimeric gag-env proteins in SF9 cells infected by recombinant baculoviruses. Recombinant baculovirus-infected SF9 cell lysates were analyzed by SDS-PAGE and proteins were stained with Coomassie blue (A) or detected by Western blots with pooled sera from AIDS patients (B), Lanes 1–4: recombinant viruses AcNPV-HIV-2gag, Ac-gagM-1V3, Ac-gagC-1V3, and Ac-gagC-1V3+1CD4. The chimeric gag-env particles released into the culture supernatant were purified by centrifugation in 20–60% discontinuous sucrose density gradients, subjected to SDS-PAGE and detected by Coomassie blue staining (C) and Western blot (D). Lane 1: Purified gag particle; Lanes 2–4: Purified gagC-1V3, gagC-2V3 and gagC-2V3+2CD4 chimeric particles; M, Marker proteins; C, uninfected cell control; Wt, wild-type AcNPV-infected cells. The major fusion protein P55 and P66 are indicated with arrows and cleavage products are indicated by open arrows.
Figure 4A:
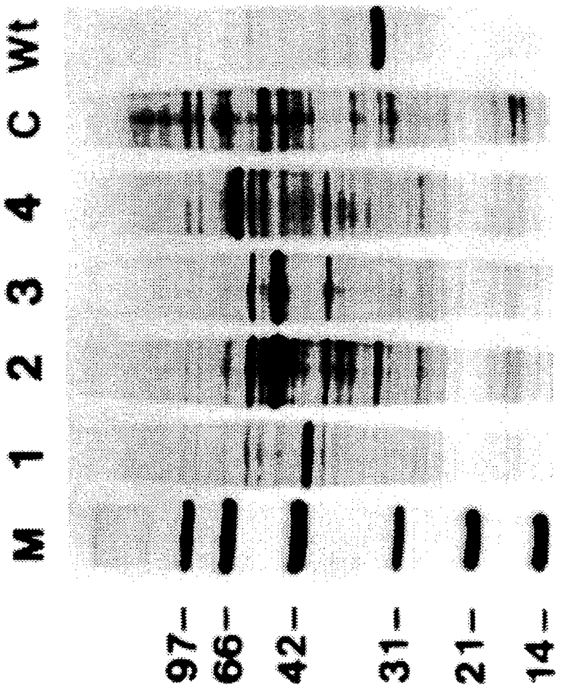
Figure 4D:
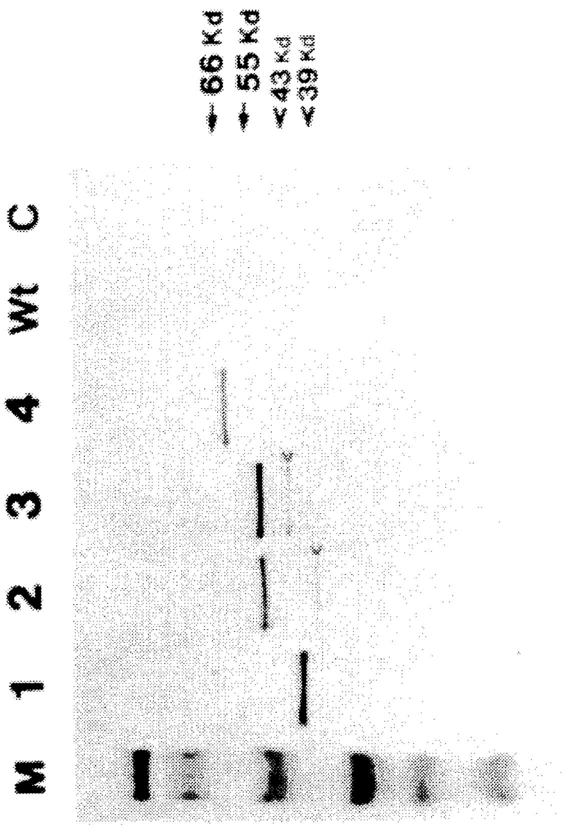
Figure 4C:
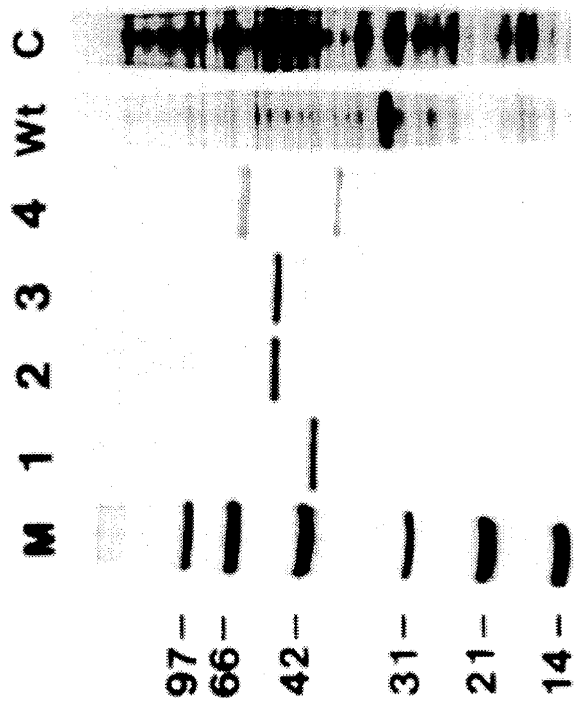
Figure 5A:
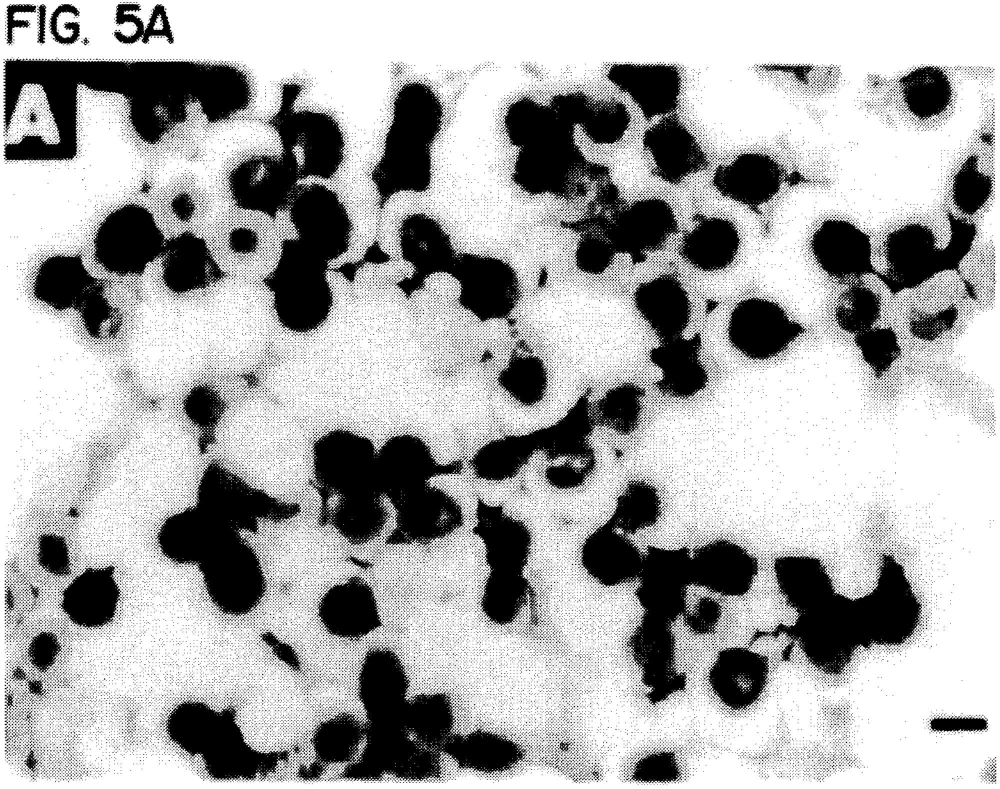
FIG. 5 shows electron micrographs of sucrose gradient-purified gag-env chimeric particles. (A) HIV-2 gag particles produced by SF9 cells infected with recombinant AcNPV-HIV-2 gag, (B) chimeric gag-env particles produced by recombinant Ac-gagC-1V3, (C) chimeric gag particles produced by recombinant Ac-gagC-2V3, and (D) chimeric gag particles produced by recombinant Ac-gagC-2V3+2CD4. Samples were stained with uranyl acetate. The bar represents 100 nm.
Figure 5B:
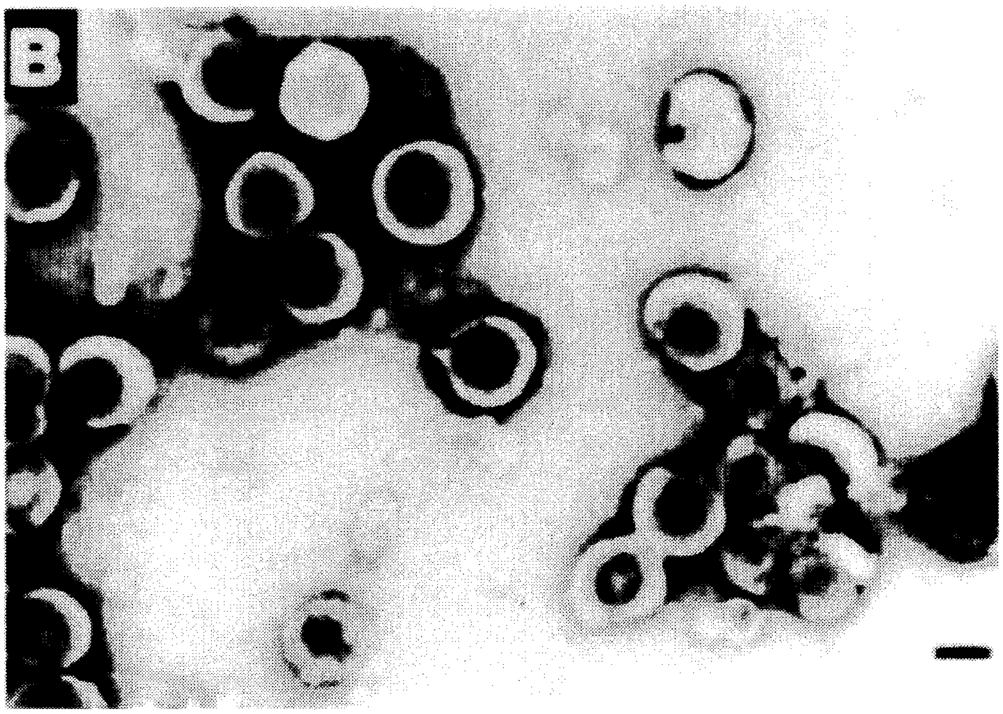
Figure 5C:
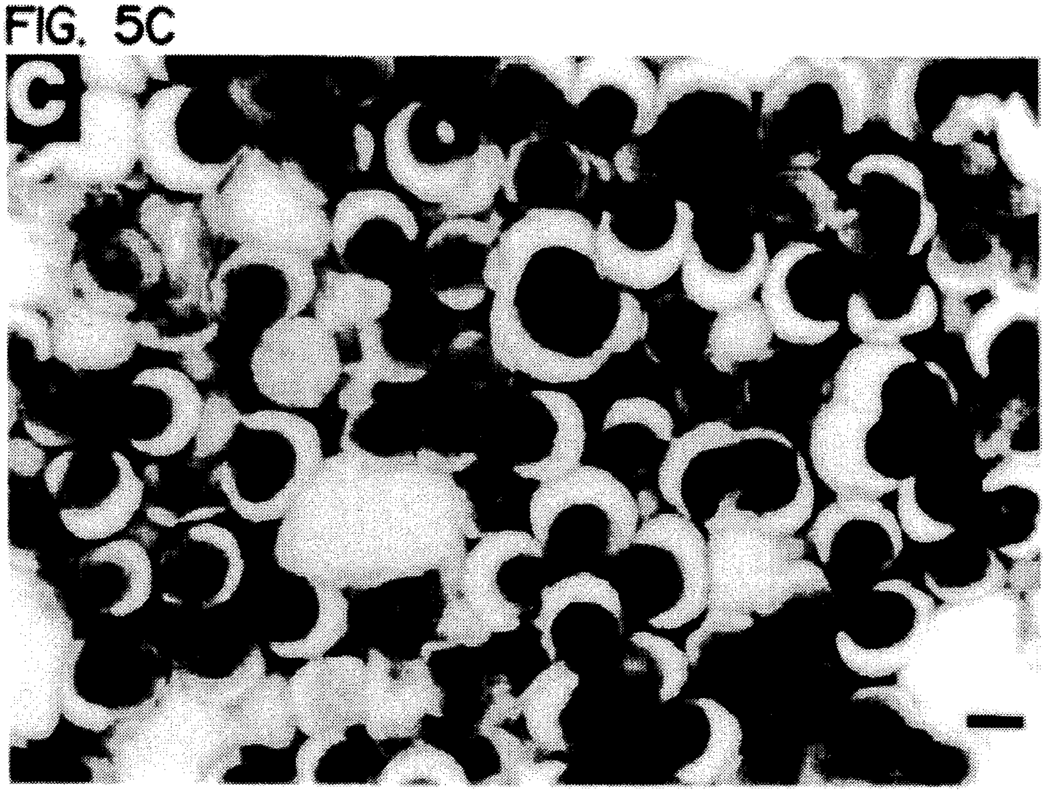
Figure 5D:
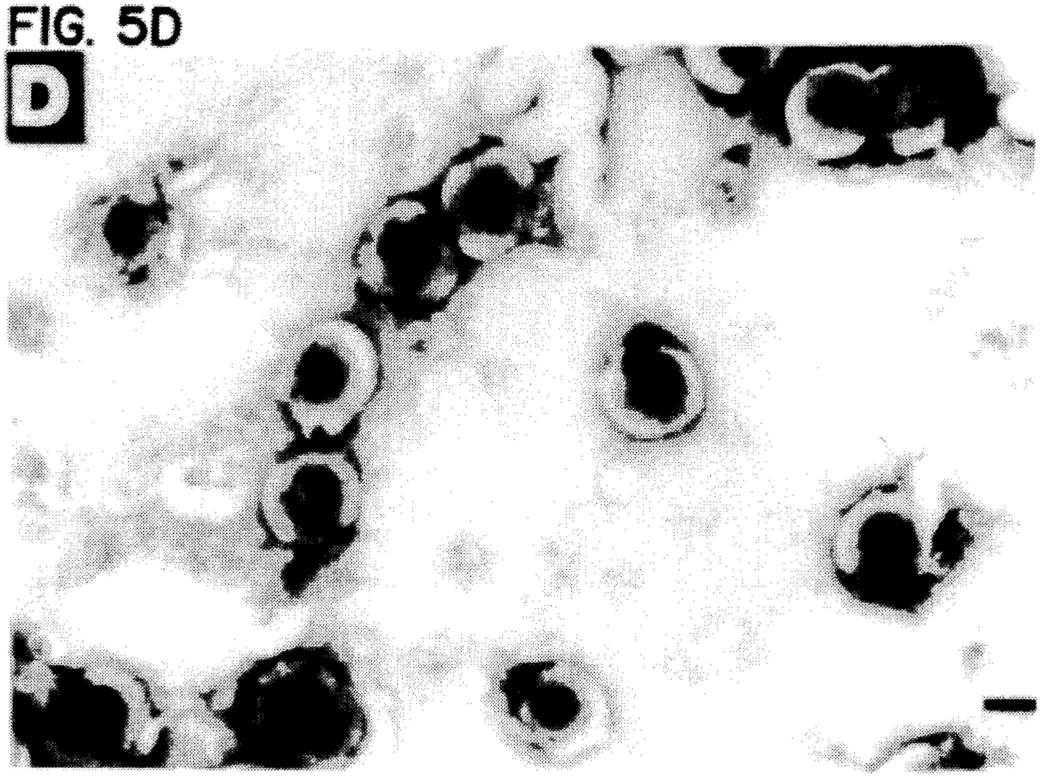

FIG. 4A shows the proteins produced by recombinant baculoviruses Ac-gagM-1V3, Ac-gagC-1V3 and Ac-gagC-1V3+1CDB4BD. Since the original HIV-2 gag protein has 93 amino acids deleted from the C-terminus, according to the invention, an insertion of V3 (91 amino acids) or V3+CD4BD (194 amino acids) of HIV-1 gp120 into the gag gene would produce proteins of 55 KDa and 66 KDa, respectively.

As shown in FIG. 4A, strongly stained protein bands migrating at either 55 KDa or 66 KDa were observed in the lysates of SF9 cells infected with Ac-gagM-1V3 (lane2), Ac-gagC-1V3 (lane3) and Ac-gagC-1V3+1CD4BD (lane 4), but were not present in lysates of mock or wild type baculovirus-infected cells. Western blot analysis revealed that both the p55 and p66 fusion proteins were recognized by pooled HIV-1 positive human sera (FIG. 4B, lanes 2, 3, and 4). No specific reaction was observed with mock and wild type AcNPV-infected cells. The results clearly demonstrate that insertion of either HIV-1 V3 or V3+CD4BD into the gag protein resulted in expression of proteins at levels at least as high as that of recombinant AcNPV-HIV-2gag alone (FIG. 4A, lane 1).

Similar results were obtained when three other recombinant baculoviruses containing the V3 and V3+CD4BD genes from HIV-2 gp120, Ac-gagM-2V3, Ac-gagC-2V3, and Ac-gagC-2V3+2CD4BD were analyzed.

EXANPLE 5

Purification of Chimeric Particles

The cell culture fluids obtained from Example 4 were collected after centrifugation at 1,000×g for 20 minutes. Chimeric particles in the culture supernatant were collected by ultracentrifugation in a Beckman SW 28 rotor at 80,000×g for 1 hour and resuspended in PBS containing 0.1% Tween 20, 10 μg/ml aprotinin, and stored at 4° C. A band containing gag particle was collected from a 20–60% discontinuous sucrose gradient, diluted at least 10-fold with PBS, and pelleted in an SW28 rotor at 80,000×g for 1 hour. The pellet was gently suspended in PBS. gagC-1V3 and gagC-2V3 particles were recovered from the 50% sucrose cushion, whereas gagC-2V3+2CD4BD chimeric particles banded on top of the 60% sucrose cushion. The results of the morphology of sucrose gradient purified particles by transmission electron microscopy using uranyl acetate staining is shown in FIG. 5.

HIV-2 gag particles were spherical (FIG. 5A), had diameters of approximately 100 nm, and were similar to those of mature HIV-1 particles budding from HIV-1 infected cells. The chimeric particles gagC-1V3 (FIG. 5B), gagC-2V3 (FIG. 5C) and gagC-2V3+2CD4BD (FIG. 5D) exhibited morphologies similar to the gag particles. The peripheral granular material frequently showed striations with a periodicity suggesting a helical arrangement. It formed a shell-like layer probably inside a lipid membrane and was presumably rigid. The only difference between the gag particles and chimeric gag particles was that the chimeric gag particles are slightly larger with approximate diameters of 130 nm, similar to the diameter of mature HIV-1 particles.

EXAMPLE 6 (EXPERIMENTAL)

Antigenicity of Chimeric gag Particles

Antigenicity of chimeric gag particles was investigated by immunoblot analysis. Purified chimeric gag particles were subjected to SDS-PAGE and analyzed by Western blotting with rabbit antisera directed against HIV-1 and HIV-2 gp120 and $^{125}$I-labeled protein A. The results are shown in FIG. 6. As shown, lane 1 is HIV-2 gag protein; lane 2, gp120 protein; lane 3, chimeric gagC-1V3 protein; lane 4, chimeric gagC-1V3+1CD4 protein; C, cell control; and Wt is wild type AcNPV-infected cell control.

Figure 6A:
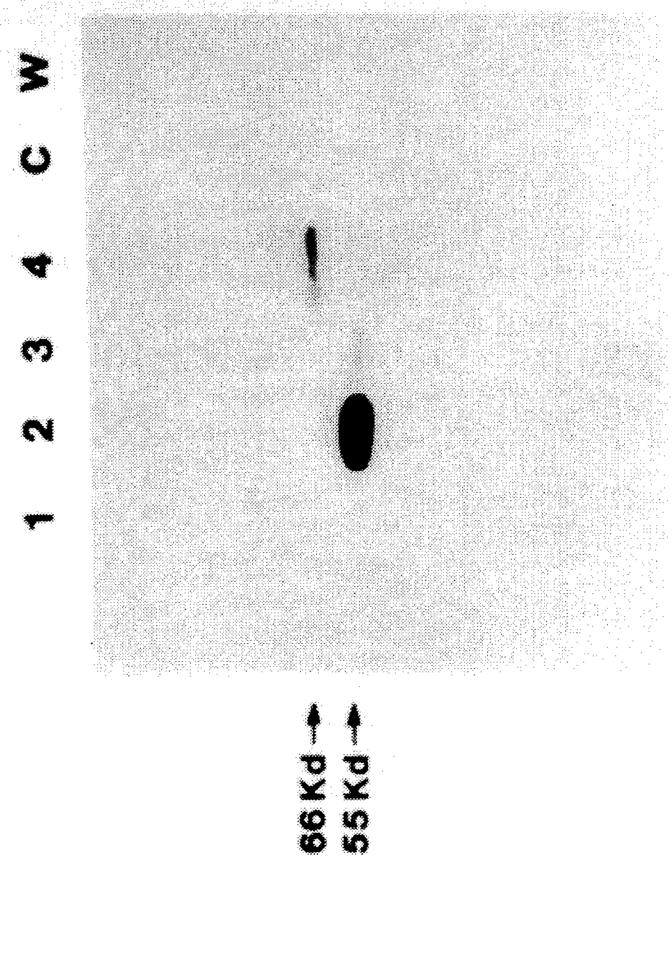
FIG. 6 shows immunoblot analysis of chimeric gag-env proteins. The chimeric gag-env proteins and gp120 of HIV-1 and HIV-2 were subjected to SDS-PAGE and electro-transferred to nitrocellulose filters. Filters were incubated with rabbit antisera specific for (A) HIV-1 gp120 and (B) HIV-2 gp120, and with $^{125}$I-labeled protein A. Lane 1:HIV-2 gag protein; lane 2, gp120 protein; lane 3, chimeric gagC-1V3 protein; lane 4, chimeric gagC-1V3+1CD4 protein; C, cell control; W, wild type AcNPV-infected cell control. The rabbit antisera against HIV-1 and HIV-2 gp120 have been described herein.
Figure 6B:
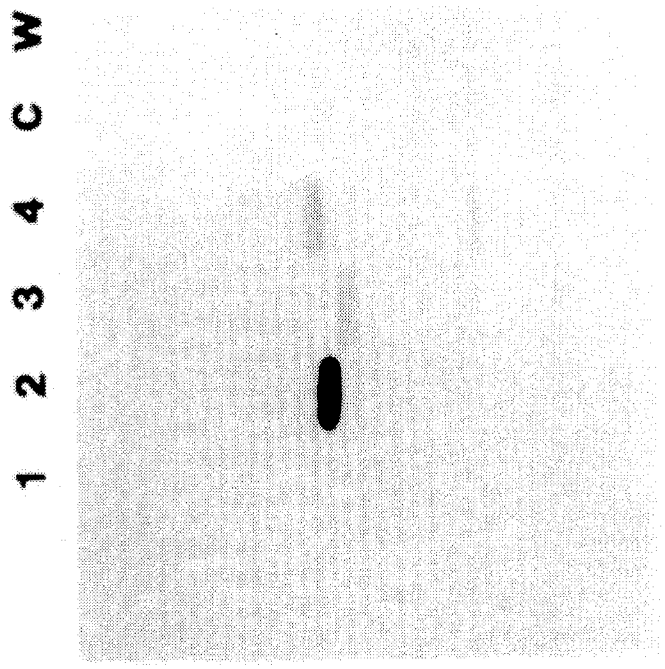

The HIV-2 gag protein was not recognized by anti-gp120 sera (FIGS. 6A and 6B, lane 1), while the nonglycosylated forms of gp120 of HIV-1 and HIV-2 showed strong reactivity with their corresponding antisera (FIGS. 6A and 6B, lane 2). The 55 KDa and 66 KDa fusion proteins were specifically recognized by rabbit antisera against HIV-1 or HIV-2 gp120s (FIGS. 6A and 6B, lanes 3 and 4). The results clearly demonstrate that the chimeric proteins can be detected by antiserum specific for gp120, and reaffirm that inserted sequences of V3 or V3+CD4BD are antigenic.

To examine the capacity of particles to induce antibodies to both gag and env proteins of HIV, rabbits were immunized four times at 4-week intervals with purified gagC-1V3 and gagC-2V3 chimeric particles. The immune rabbit sera were collected 2 weeks after the last immunization and tested for their ability to recognize gp120 of HIV-1 and HIV-2.

Figure 7B:
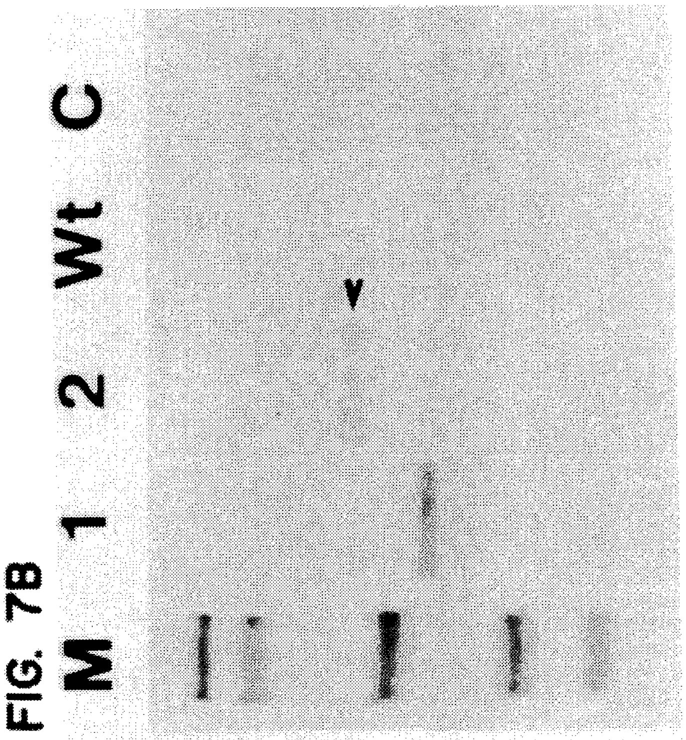
FIG. 7 shows Western blot analysis using rabbit antisera made against chimeric gag-env particles. (A) Anti-gagC-1V3 serum recognized non-glycosylated gp120 protein of HIV-1; Lane 1, HIV-2 gag protein; Lane 2, non-glycosylated gp120 protein of HIV-1. (B) Anti-gagC-2V3 serum recognized non-glycosylated gp120 protein of HIV-2; Lane 1, HIV-2 gag protein; lane 2, non-glycosylated gp120 protein of HIV-2. Wt, wild-type AcNPV-infected cells at day 3 post-infection (p.i.); C, cell control. Sera were diluted 1:200, and a Bio-Rad Immuno-Blot AK detection system was employed.
Figure 7A:
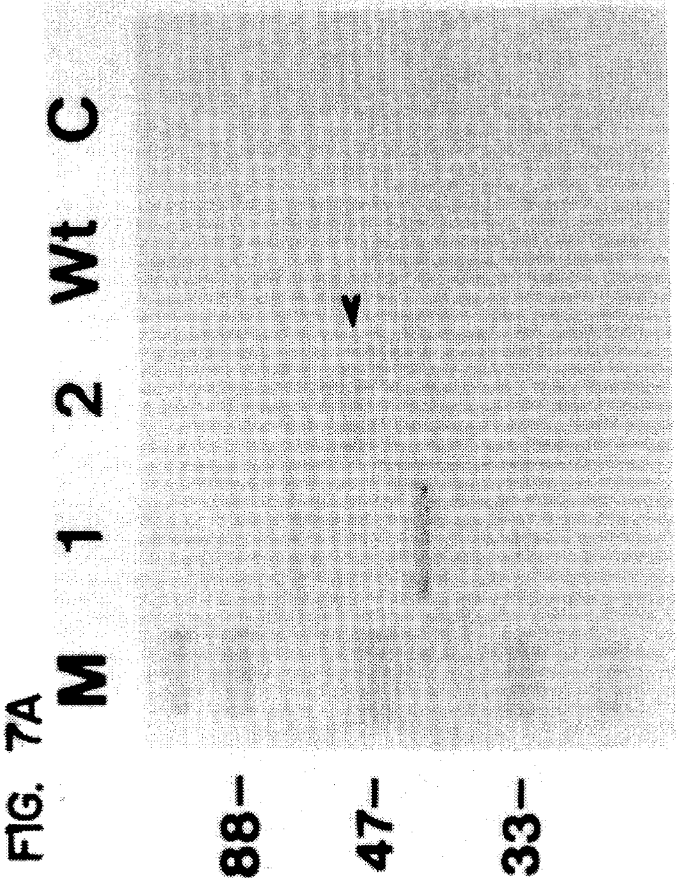
Figure 8A:
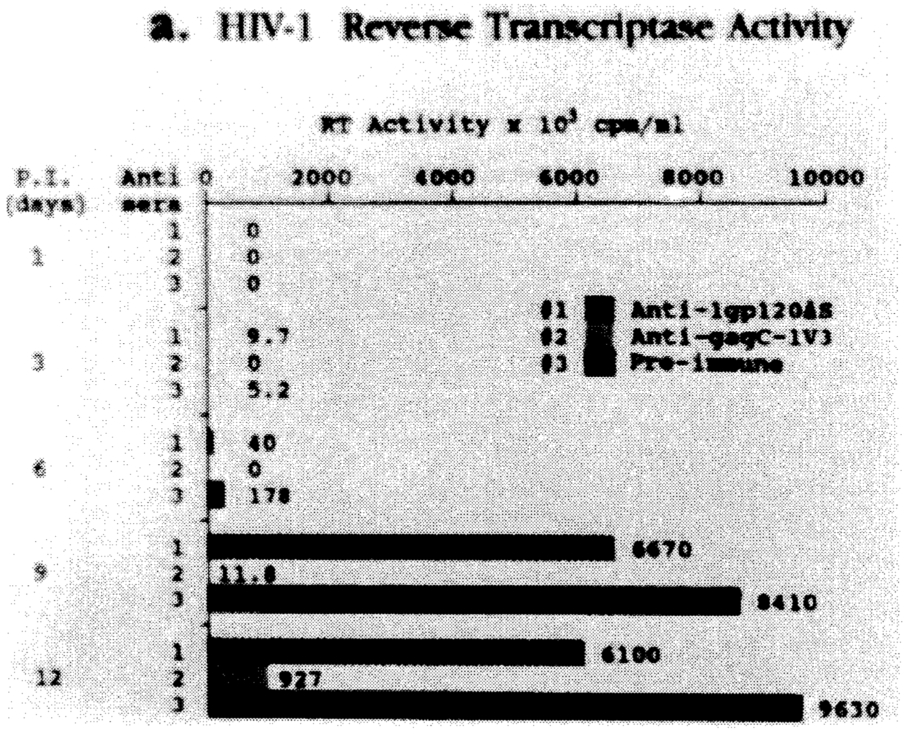
FIG. 8 shows neutralization of HIV-$1_{IIIB}$ and HIV-$2_{ROD}$ infection with immune rabbit sera. Antisera against gagC-1V3 and gagC-2V3(HIV-2) chimeric particles were diluted and tested for neutralization of virus using reverse transcriptase and viral p24 or p26 assays. (a) and (b): HIV-1; (c) and (d): HIV-2. Pre-immune serum (); V3-specific immune serum () from rabbits immunized with chimeric gag-V3 particles of HIV-1 or HIV-2; anti-gp120 sera () specific for gp120 of HIV-1 or HIV-2. The neutralizing activity of anti-gagC-1V3 and anti-gagC-2V3 sera were determined by incubation of sera (1:5 dilution) with stock virus preparation of HIV-$1_{IIIB}$ (5000 $TCID_{50}$) or HIV-$2_{ROD}$ (8000 $TCID_{50}$) at 37° C. for 1 hour before infecting H9 cell. Viral infection was monitored by reverse transcriptase activity (a and c) and the production of HIV-1 p24(b) or HIV-2 p26(d) gag proteins at 1–16 days post-infection (p.i.).
Figure 8B:
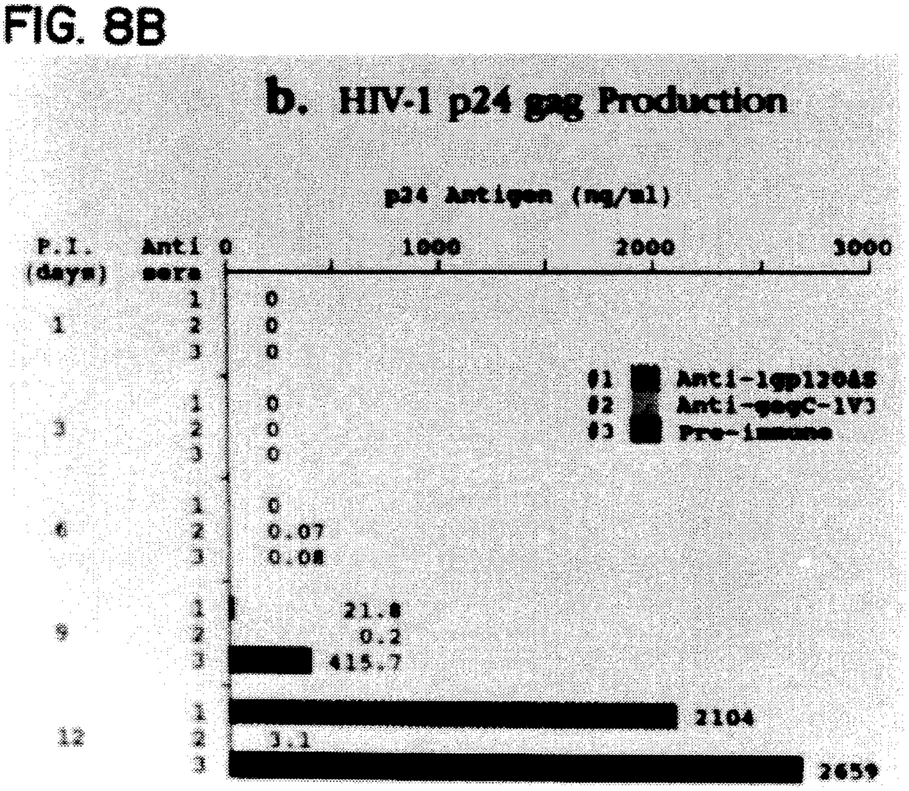
Figure 8C:
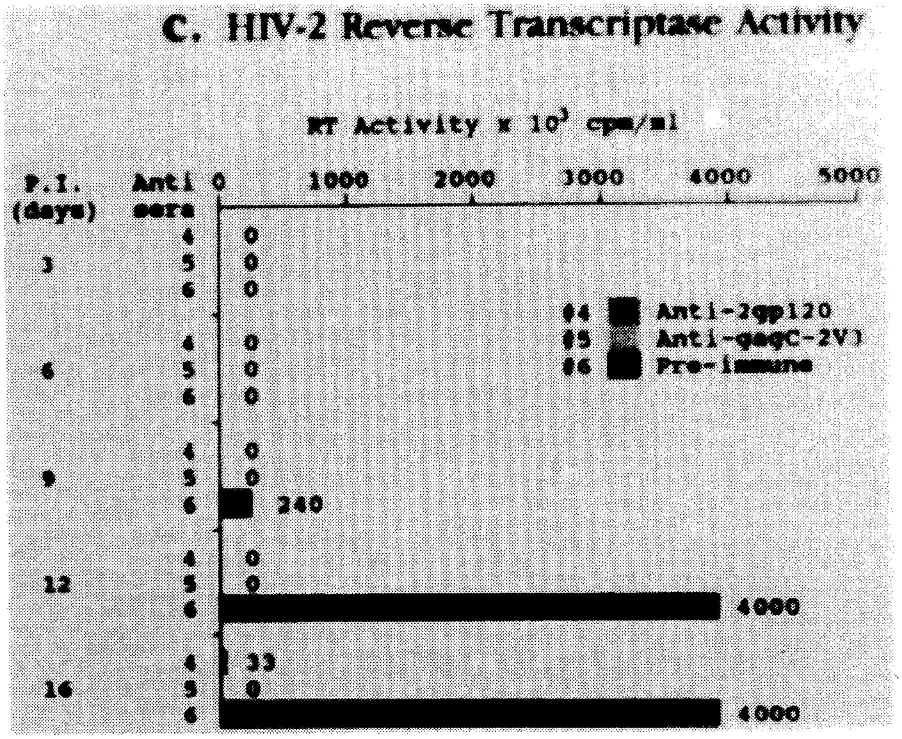
Figure 8D:
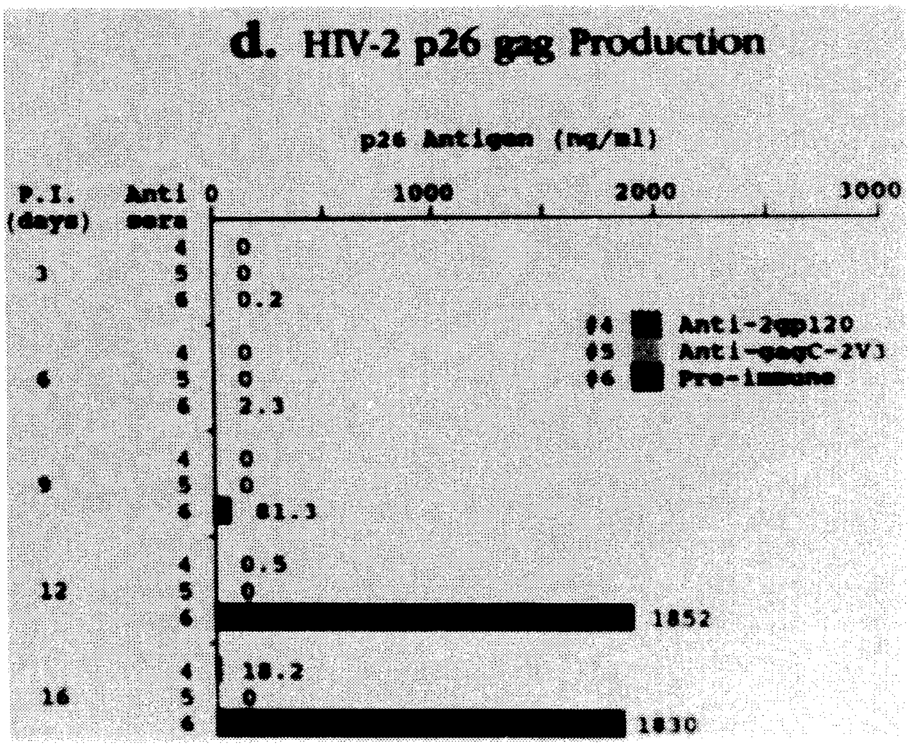

As shown in FIG. 7, the antisera made against both gagC-1V3 and gagC-2V3 chimeric particles recognized not only carrier HIV-2 gag protein (FIGS. 7A, 7B, lanes 1) but also non-glycosylated gp 120 of HIV-1 (FIG. 7A, lane 2) and HIV-2 (FIG. 7B, lane 2).

In contrast, neither wild type AcNPV infected SF9 cells nor uninfected SF9 cells contain proteins which were recognized by the antisera. These results clearly demonstrate that the V3 loop domain in chimeric gagC-1V3 and gagC-2V3 particles retain both antigenic and immunogenic properties.

EXAMPLE 7 (EXPERIMENTAL)

Immune Sera Against Chimeric gag-V3 Particles of HIV-1 or HIV-2 Neutralize Virus Infectivity in Vitro Rabbit anti-sera directed against chimeric particles were used to neutralize the infectivity of HIV as assayed by reverse transcriptase (RT) activity and gag p24 production. Rabbits were immunized four times at one month intervals with intramuscular injections of 25 µg of the density gradient-purified chimeric gag particles. Rabbit anti-gagC-1V3 and anti-gagC-2V3 sera (25 µg) were mixed with 100 µl of virus which represented 5000 $TCID_{50}$ of HIV-$1_{IIIB}$ or 8000 $TCID_{50}$ of HIV-$2_{ROD}$, respectively, and the mixtures were used to infect H9 cells. The amount of p24 gag protein and reverse transcriptase (RT) activity in the culture media were assayed as quantitation of virus production on different days after infection (days 1–16), and the levels were compared with those of control samples in which virus was incubated with pre-immune sera or rabbit anti-gp120 serum.

FIG. 8 shows that both rabbit anti-gagC-1V3 and anti-gagC-2V3 sera contained antibodies capable of neutralizing HIV infection of H9 cells. By day 9 post-infection, antisera to gagC-1V3 and gagC-2V3 chimeric particles completely blocked the production of HIV-1 and HIV-2, respectively. However, at day 12 post-infection, a small amount of HIV-1 was detected in cultures treated with anti-gagC-1V3 serum (FIG. 8, *a* and *b*). In contrast, the antisera to gagC-2V3 chimeric particles completely neutralized HIV-2 infectivity (FIG. 8, *c* and *d*). No reduction in RT and p24 gag protein production were observed with pre-immune sera. Rabbit anti-gp120 sera of HIV-2 showed stronger neutralizing activity of HIV-$1_{ROD}$ than rabbit anti-gp120 sera of HIV-1 against HIV-$1_{IIIB}$ (FIG. 8).

From the above, it is recognized that the chimeric protein according to the present invention showed excellent neutralizing activity against HIV-1 and HIV-2.

EXAMPLE 8

Construction of a gag-env Chimeric Gene Which Includes Multiple Virus-neutralizing Domains from Both gp120 and gp41

Recent observations indicate that there are four major neutralizing regions of HIV-1 envelope glycoproteins (Broliden et al. Proc. Natl. Acad. Sci. USA, 89:461, 1992). The neutralizing domains include (1) the strain-specific third-variable (V3) regions of gp120 (amino acids 304–318), (2) the C-terminal end of gp120 (amino acids 489–508), (3) the conserved region of gp41 (amino acids 652–666), and (4) the conserved region in the intracellular part of gp41 (amino acids 732–746). Peptides corresponding to these four regions have been found to inhibit neutralization mediated by serum from HIV-1 antibody positive individuals.

Figure 9A:
FIG. 9A shows a chimeric gag-env gene containing four neutralizing epitopes of HIV-1, each 15 amino acids, at the 3' terminus of the gag gene; #1, amino acids 304–318 (V3); #2, amino acids 489–503 (C-terminus of gp120); #3, amino acids 652–666 (gp41); #4, amino acids 732–746 (gp41).
Figure 14:
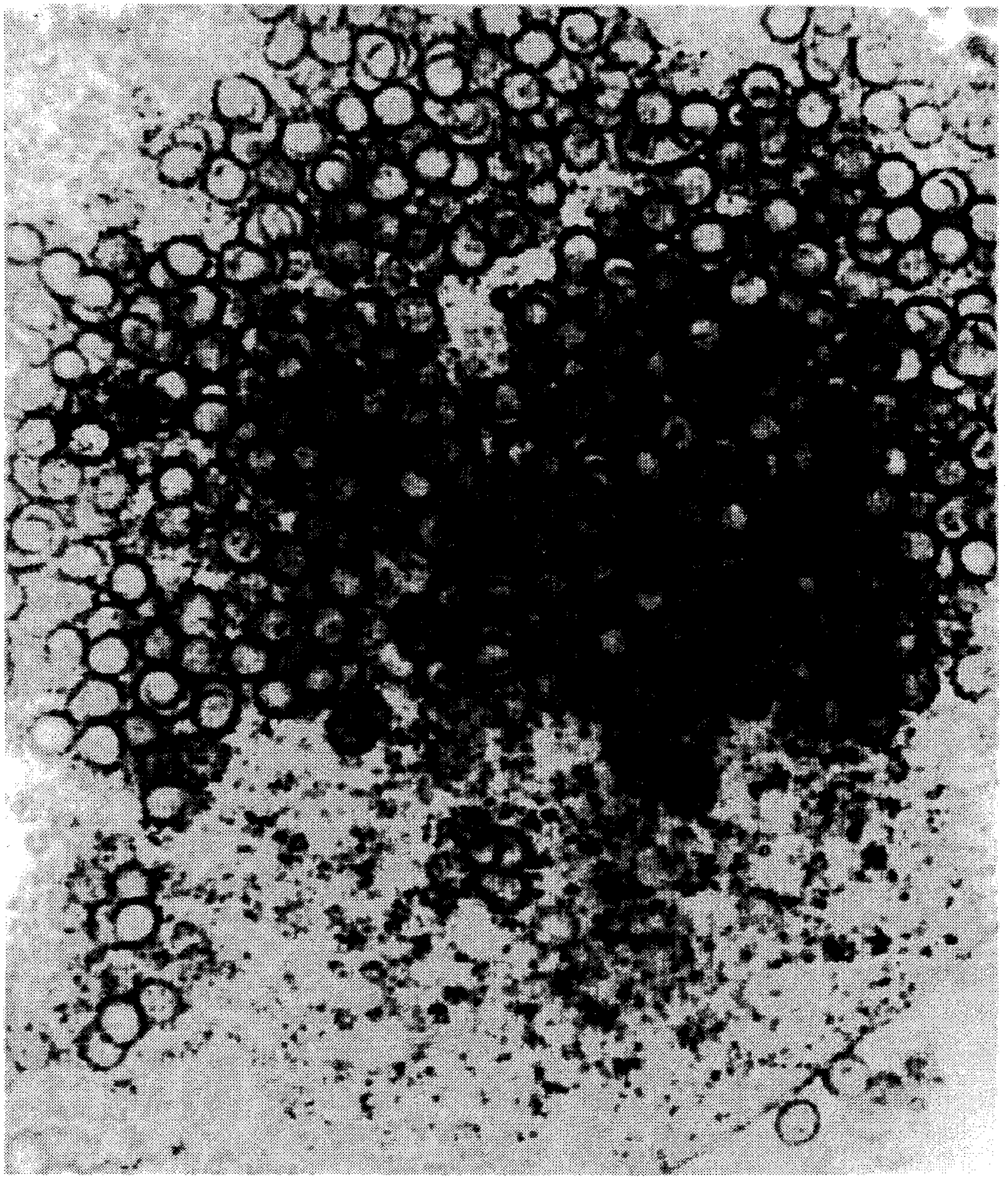
FIG. 14 shows a thin-section electronmicrograph of virus-like particles formed by the various constructs.

The coding sequences of the four neutralizing epitopes were synthesized on the basis of HIV-$1_{mn}$ strain sequence (Carrow et al., *AIDS Res. and Hum. Retroviruses* 7:831, 1991). It has been shown that antibodies to HIV-$1_{mn}$ gp120 are most prevalent in Africans and Americans (Katzenstein et al., *J. AIDS* 3:810, 1990). A chimeric gag-env gene was constructed which contained the four neutralizing epitopes attached at the 3' terminus of HIV-2 gag gene, as shown in FIGS. 9 and 10A (construct A). A recombinant baculovirus, *Autobiographa californica* nuclear polyhedrosis virus (Ac2gag4NDYK virus) containing Construct A, has been placed on deposit with ATCC on Jul. 28, 1993, under ATCC accession number VR2423. Construct A produced virus-like particles as shown in FIG. 14, and induced neutralizing antibodies.

EXAMPLE 9

Figure 9B:
FIG. 9B shows a consensus sequence (CS) of HIV-1 V3 loop in tandem; TRKSIHIGPGRAFYTTGE [SEQ ID NO:6], triple repeats of 18 amino acids (18×3=54 amino acids).

Construction of a gag-env Chimerio Gene Which Contains Multiple V3 Coding Sequences from the Consensus Sequence of HIV-1 V3 loop It has been shown that HIV-1 infected individuals from South America, Africa and North America share a common pattern of neutralizing antibody responses to different virus strains, with a striking predominance of HIV-$1_{mn}$ seroreactivity. This reactivity is due in part to antibodies directed against the V3 region of gp120. (Carrow et al., *AIDS Res. and Hum. Retroviruses* 7:831, 1991; Katzenstein et al., *J. AIDS* 3:810, 1990). In this example, multiple copies were constructed of the consensus sequences of V3 region in tandem, as shown in FIGS. 9B and 10B (construct B) to enhance immune responses. These constructs represent the HIV-$1_{mn}$ strain, a prevalent strain worldwide. A recombinant baculovirus, *Autobiographa californica* nuclear polyhedrosis virus (Ac2gag3CSV3YK virus) containing Construct B, has been placed on deposit with ATCC on Jul. 28, 1993, under ATCC accession number VR2425. Construct B also produced identical virus-like particles as Construct A, and as shown in FIG. 14. However, chimeric construct B (FIG. 10B) provided a much stronger immune response.

EXAMPLE 10

Figure 9C:
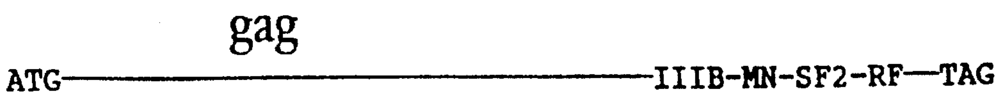
FIG. 9C shows a gag-env chimeric gene construct containing multiple V3 domains from different HIV-1 isolates (V3); IIIB, MN, SF2, RF, each 15 amino acids.

Construction of a gag-env Chimeric Gene Which Contains Multiple Distinct V3 Coding Sequences of Major HIV-1 Variants Isolates of HIV-$1_{IIIB}$, HIV-$1_{mn}$, $HIV_{SF2}$, HIV-$1_{RF}$ and HIV-$2_{NIH\text{-}Z}$ were selected to construct a gag-env chimeric gene containing several V3 domains, as shown in FIGS. 9C, 11, 12 and 13. Antibodies made against these multiple epitopes are capable of interacting with and neutralizing most variants of HIVs which are naturally transmitted in the population. While both the V3 region and gag proteins contain both helper T lymphocyte and cytotoxic T lymphocyte epitopes and may therefore be capable of independent function as immunogens, in this example, multiple V3 loop sequences were linked to HIV-2 gag sequence to provide a larger antigen for expression and to increase the potential for the induction of T helper and cytotoxic effectors. The scheme of linking multiple V3 epitopes is illustrated in FIGS. 9C and 11. Sequences for these constructs are shown in FIGS. 12 and 13 A recombinant baculovirus, *Autobiographa californica* nuclear polyhedrosis virus (Ac2gag3CSV3YK virus) containing Construct C, has been placed on deposit with ATCC on Jul. 28, 1993, under ATCC accession number VR2424. These constructs also formed virus-like particles indistinguishable from those provided by construct A (FIG. 10A), as shown in FIGS. 5 and 14.

What is claimed is:

1. A recombinant, chimeric, immunogenic gag-env virus-like particle of human immunodeficiency virus (HIV), comprising:

(i) an HIV-2 Gag protein which extends from the amino terminus of Gag to a minimum of amino acid 376 and a maximum of amino acid 425, such that said Gag protein is capable of forming virus-like particles; and, (ii) an HIV Env protein linked to the C-terminus of Gag containing at least one virus-neutralizing epitope.

2. The recombinant, chimeric, immunogenic HIV gag-env virus-like particle according to claim 1, wherein the gag coding region includes at least one proline residue at amino acid positions 373, 375, or 377.

3. The recombinant, chimeric, immunogenic HIV gag-env virus-like particle according to claim 1, wherein the env gene encodes for a 198 amino acid segment containing the HIV-2 V3 loop and CD4 binding domain, and the gag-env coding region comprises 574–623 amino acids.

4. The recombinant, chimeric, immunogenic HIV gag-env virus-like particle according to claim 1, wherein the env gene encodes for the V3 loop of HIV gp120, the CD4-binding domain of HIV gp120, or a combination thereof.

5. The recombinant, chimeric, immunogenic HIV gag-env virus-like particle according to claim 4, wherein the env gene encodes for a 91 amino acid segment containing the HIV-1 gp120 V3 loop; a 90 amino acid segment containing the HIV-2 gp120 V3 loop; or a 198 amino acid segment containing the HIV-2 V3 loop and CD4-binding domain.

6. The recombinant, chimeric, immunogenic HIV gag-env virus-like particle according to claim 1, wherein the env gene encodes for at least two HIV-1 gp120 V3 loops placed in tandem.

7. The recombinant, chimeric, immunogenic HIV gag-env virus-like particle according to claim 6, wherein at least two of the HIV-1 gp120 V3 loops correspond to different viral isolates.

8. A method for the detection of antibodies directed against human immunodeficiency virus (HIV) in human biological specimens, comprising:

(i) immobilizing the recombinant, chimeric, immunogenic HIV gag-env virus-like particle of claim 1 on a solid support;

(ii) contacting said recombinant particle with a human biological specimen and allowing immobilized antigen-antibody complex formation to occur;

(iii) washing away unbound antibodies and antigens from the immune complexes of step (ii); and (iv) detecting said immune complexes by the addition of a second labeled anti-human antibody.

* * * * *

UNITED STATES PATENT AND TRADEMARK OFFICE
CERTIFICATE OF CORRECTION

PATENT NO. : 5,580,773

DATED : December 3, 1996

INVENTOR(S) : Kang et al.

It is certified that error appears in the above-identified patent and that said Letters Patent is hereby corrected as shown below:

On the title page,

[56], line References Cited: "6/1990" should read --5/1990--

[56], line References Cited, Other Publications: insert "," after "Neurath, A. R. et al."

[56], line References Cited, Other Publications: "Molecular Immunology" should read as --*Molecular Immunology*--

[56], line References Cited, Other Publications: "529-49" should read --539-549--

Col. 7, line 2: "Autographa Californica" should read as --*Autographa Californica*--

Col. 7, line 60: "Autographa Californica" should read as --*Autographa Californica*--

Col. 11, line 31: "(25 μg)" should read --(25 μl)--

Signed and Sealed this

Eighteenth Day of November 1997

Attest:

BRUCE LEHMAN

*Attesting Officer* *Commissioner of Patents and Trademarks*

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Human immunodeficiency virus type 1

( x i ) SEQUENCE DESCRIPTION: SEQ ID NO:1:

CGAAGATCTG TCAATTTCAC GG 22

( 2 ) INFORMATION FOR SEQ ID NO:2:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Human immunodeficiency virus type 1

( x i ) SEQUENCE DESCRIPTION: SEQ ID NO:2:

GCAGATCTTT GCTTAAAGAT TA 22

( 2 ) INFORMATION FOR SEQ ID NO:3:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Human immunodeficiency virus type 2

( x i ) SEQUENCE DESCRIPTION: SEQ ID NO:3:

CGAGATCTCA TTGTAAGAGG CC 22

( 2 ) INFORMATION FOR SEQ ID NO:4:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:

( A ) ORGANISM: Human immunodeficiency virus type 2

( x i ) SEQUENCE DESCRIPTION: SEQ ID NO:4:

GCAGATCTTC TGCAGTTAGT CC 22

( 2 ) INFORMATION FOR SEQ ID NO:5:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Human immunodeficiency virus type 2

( x i ) SEQUENCE DESCRIPTION: SEQ ID NO:5:

GCAGATCTCT TTACTGATGT AG 22

( 2 ) INFORMATION FOR SEQ ID NO:6:

( i ) SEQUENCE CHARACTERISTICS:
( A ) LENGTH: 18 amino acids
( B ) TYPE: amino acid
( D ) TOPOLOGY: linear ( i i ) MOLECULE TYPE: peptide ( v i i ) IMMEDIATE SOURCE:
( B ) CLONE: Consensus Sequence (CS) of HIV-1 V3 loop ( x i ) SEQUENCE DESCRIPTION: SEQ ID NO:6:

Thr Arg Lys Ser Ile His Ile Gly Pro Gly Arg Ala Phe Tyr Thr Thr
1 5 10 15

Gly Glu ( 2 ) INFORMATION FOR SEQ ID NO:7:

( i ) SEQUENCE CHARACTERISTICS:
( A ) LENGTH: 194 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: HIV-1 Four Neutralizing Epitopes ( x i ) SEQUENCE DESCRIPTION: SEQ ID NO:7:

AGAAAAAGCA TCCGTATCCA GAGAGGACCA GGGAGAGCAT TTGTTGTAAA AATTGAACCA 60

TTAGGAGTAG CACCCACCAA GGCAAAGAGA CAGCAAGAAA AGAATGAACA AGAATTATTG 120

GAATTAGATA AATGGGGAAT AGAAGAAGAA GGTGGAGAGA GAGACAGAGA CAGATCCATT 180

TAGGGATCCG CATG 194

( 2 ) INFORMATION FOR SEQ ID NO:8:

( i ) SEQUENCE CHARACTERISTICS:
( A ) LENGTH: 176 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:

-continued ( A ) ORGANISM: Consensus Sequence of HIV-1 V3 Loop ( x i ) SEQUENCE DESCRIPTION: SEQ ID NO:8:

ACCAGAAAAA GCATCCATAT CGGACCAGGG AGAGCATTTT ATACAACAGG AGAAACCAGA 60

AAAAGCATCC ATATCGGACC AGGGAGAGCA TTTTATACAA CAGGAGAAAC CAGAAAAAGC 120

ATCCATATCG GACCAGGGAG AGCATTTTAT ACAACAGGAG AATAGGGATC CGCATG 176

( 2 ) INFORMATION FOR SEQ ID NO:9:

( i ) SEQUENCE CHARACTERISTICS:
( A ) LENGTH: 194 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: V3 Loop of Different HIV-1 Isolates ( x i ) SEQUENCE DESCRIPTION: SEQ ID NO:9:

AGCATCCGTA TCCAGAGAGG ACCAGGGAGA GCATTTGTTA CAATCAAAAG AATCCATATC 60

GGACCAGGGA GAGCATTTTA TACAACAAAG AGCATCACAA AGGGACCAGG GAGAGTAATC 120

TATGCCACAG GACAGAGCAT CTATATCGGA CCAGGGAGAG CATTTCATAC AACAGGGAGA 180

TAGGGATCCG CATG 194

( 2 ) INFORMATION FOR SEQ ID NO:10:

( i ) SEQUENCE CHARACTERISTICS:
( A ) LENGTH: 386 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Double Construct C1

( x i ) SEQUENCE DESCRIPTION: SEQ ID NO:10:

AGCATCCGTA TCCAGAGAGG ACCAGGGAGA GCATTTGTTA CAATCAAAAG AATCCATATC 60

GGACCAGGGA GAGCATTTTA TACAACAAAG AGCATCACAA AGGGACCAGG GAGAGTAATC 120

TATGCCACAG GACAGAGCAT CTATATCGGA CCAGGGAGAG CATTTCATAC AACAGGGAGA 180

GATATCAGAT CTAGCATCCG TATCCAGAGA GGACCAGGGA GAGCATTTGT TACAATCAAA 240

AGAATCCATA TCGGACCAGG GAGAGCATTT TATACAACAA AGAGCATCAC AAAGGGACCA 300

GGGAGAGTAA TCTATGCCAC AGGACAGAGC ATCTATATCG GACCAGGGAG AGCATTTCAT 360

ACAACAGGGA GATAGGGATC CGCATG 386

( 2 ) INFORMATION FOR SEQ ID NO:11:

( i ) SEQUENCE CHARACTERISTICS:
( A ) LENGTH: 577 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Triple Construct C1

( x i ) SEQUENCE DESCRIPTION: SEQ ID NO:11:

AGCATCCGTA TCCAGAGAGG ACCAGGGAGA GCATTTGTTA CAATCAAAAG AATCCATATC 60

GGACCAGGGA GACGATTTTA TACAACAAAG AGCATCACAA AGGGACCAGG GAGAGTAATC 120

TATGCCACAG GACAGAGCAT CTATATCGGA CCAGGGAGAG CATTTCATAC AACAGGGAGA 180

GATATCGCTG CAGCATCCGT ATCCAGAGAG GACCAGGGAG AGCATTTGTT ACAATCAAAA 240

GAATCCATAT CGGACCAGGG AGAGCATTTT ATACAACAAA GAGCATCACA AAGGGACCAG 300

GGAGAGTAAT CTATGCCACA GGACAGAGCA TCTATATCGG ACCAGGGAGA GCATTTCATA 360

CAACAGGGAG AGATATCAGA TCTAGCATCC GTATCCAGAG AGGACCAGGG AGAGCATTTG 420

TTACAATCAA AAGAATCCAT ATCGGACCAG GGAGAGCATT TTATACAACA AAGAGCATCA 480

CAAAGGGACC AGGGAGAGTA ATCTATGCCA CAGGACAGAG CATCTATATC GGACCAGGGA 540

GAGCATTTCA TACAACAGGG AGATAGGGAT CCGCATG 577

( 2 ) INFORMATION FOR SEQ ID NO:12:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: HIV2-gag425

( x i ) SEQUENCE DESCRIPTION: SEQ ID NO:12:

AATTCGGATC CTATAAATAT GGGCGCGAGA AAC 33

( 2 ) INFORMATION FOR SEQ ID NO:13:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: HIV2-gag388

( x i ) SEQUENCE DESCRIPTION: SEQ ID NO:13:

CCGCGCGGAT CCCTACTTGA TTGTCCT 27

( 2 ) INFORMATION FOR SEQ ID NO:14:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: HIV2-gag380

( x i ) SEQUENCE DESCRIPTION: SEQ ID NO:14:

GCGCGGATCC CTATGCTGCG AATGGGAT 28

( 2 ) INFORMATION FOR SEQ ID NO:15:

( i ) SEQUENCE CHARACTERISTICS:
( A ) LENGTH: 29 base pairs
( B ) TYPE: nucleic acid ( C ) STRANDEDNESS: single
( D ) TOPOLOGY: linear ( i i ) MOLECULE TYPE: DNA (genomic)

( v i ) ORIGINAL SOURCE:
( A ) ORGANISM: HIV2-gag376

( x i ) SEQUENCE DESCRIPTION: SEQ ID NO:15:

GCGCCGGATC CCTAGATGGG GGCTCCTGC 29

( 2 ) INFORMATION FOR SEQ ID NO:16:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: HIV2-gag372

( x i ) SEQUENCE DESCRIPTION: SEQ ID NO:16:

GCGCGGATCC CTATGCCATG GCCTCCTT 28

( 2 ) INFORMATION FOR SEQ ID NO:17:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: HIV2-gag366

( x i ) SEQUENCE DESCRIPTION: SEQ ID NO:17:

GCGCGGATCC CTAGGCTTCT GCCTATAA 28

( 2 ) INFORMATION FOR SEQ ID NO:18:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: HIV2-gag322

( x i ) SEQUENCE DESCRIPTION: SEQ ID NO:18:

GCGCGGATCC CTATAGCAGT GTTTGGGT 28

( 2 ) INFORMATION FOR SEQ ID NO:19:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: HIV2-gag304

-continued ( x i ) SEQUENCE DESCRIPTION: SEQ ID NO:19:

GCGCGGATCC CTACAAGCTT TTGTAGAA 28